US009891302B2

(12) United States Patent
Topgaard et al.

(10) Patent No.: US 9,891,302 B2
(45) Date of Patent: Feb. 13, 2018

(54) METHOD FOR QUANTIFYING ISOTROPIC DIFFUSION AND/OR ANISOTROPIC DIFFUSION IN A SAMPLE

(71) Applicant: CR Development AB, Lund (SE)

(72) Inventors: Daniel Topgaard, Lund (SE); Samo Lasic, Lund (SE); Markus Nilsson, Oxie (SE)

(73) Assignee: CR DEVELOPMENT AB (SE)

( * ) Notice: Subject to any disclaimer, the term of this patent is extended or adjusted under 35 U.S.C. 154(b) by 0 days.

(21) Appl. No.: 15/117,770

(22) PCT Filed: Feb. 10, 2015

(86) PCT No.: PCT/SE2015/050156
§ 371 (c)(1),
(2) Date: Aug. 10, 2016

(87) PCT Pub. No.: WO2015/119569
PCT Pub. Date: Aug. 13, 2015

(65) Prior Publication Data
US 2016/0356873 A1 Dec. 8, 2016

Related U.S. Application Data

(60) Provisional application No. 61/937,941, filed on Feb. 10, 2014.

(51) Int. Cl.
*G01R 33/563* (2006.01)
*G01R 33/56* (2006.01)
(Continued)

(52) U.S. Cl.
CPC ........ *G01R 33/56341* (2013.01); *A61B 5/055* (2013.01); *G01N 24/08* (2013.01); *G01R 33/5608* (2013.01)

(58) Field of Classification Search
CPC .............. G01R 33/56341; G01R 33/56; G01R 33/56308; G01R 33/5608; G01N 24/08
(Continued)

(56) References Cited

U.S. PATENT DOCUMENTS 6,228,540 B1 * 5/2001 Kobayashi ................ G03F 1/68
430/330
2003/0160612 A1 8/2003 Yablonskiy et al.
(Continued)

FOREIGN PATENT DOCUMENTS

WO WO 2013/165312 A1 11/2013
WO WO 2013/165313 A1 11/2013

OTHER PUBLICATIONS

W.S. Price, NMR studies of translational motion, Cambridge University Press, Cambridge, (2009). pp. 72-77 and 164-166.*
(Continued)

*Primary Examiner* — Melissa Koval
*Assistant Examiner* — Rishi Patel
(74) *Attorney, Agent, or Firm* — Condo Roccia Koptiw LLP

(57) ABSTRACT

According to an aspect of the present inventive concept there is provided a method for quantifying isotropic diffusion and/or anisotropic diffusion in a sample, the method comprising: performing diffusion weighted magnetic resonance measurements on the sample using diffusion encoding magnetic gradient pulse sequences $G_{i=1...m}$, wherein each magnetic gradient pulse sequence $G_i$ is generated such that a diffusion encoding tensor $b_i$ for the magnetic gradient pulse sequence $G_i$ has one to three non-zero eigenvalues, where $b_i$=Formula (I), $q_i(t)$ is proportional to Formula (II) and t is an echo time. The method further comprises collecting data representing magnetic resonance echo signals resulting from the measurements on the sample, wherein at
(Continued)

US 9,891,302 B2

Page 2 least a subset of the data represents echo signals being acquired with a set of magnetic gradient pulse sequences causing anisotropic diffusion weighting, and wherein the diffusion encoding tensor for each gradient pulse sequence of the set of magnetic gradient pulse sequences has three non-zero eigenvalues, at least one of the three eigenvalues being different from the other two eigenvalues. The method further comprises calculating a degree of isotropic diffusion and/or a degree of anisotropic diffusion using the data.

20 Claims, 4 Drawing Sheets

(51) Int. Cl.
  G01N 24/08 (2006.01)
  A61B 5/055 (2006.01)
(58) Field of Classification Search
  USPC .......................... 324/307, 309; 600/410, 413
  See application file for complete search history.

(56) References Cited

U.S. PATENT DOCUMENTS

| | | | |
|---|---|---|---|
| 2005/0007100 | A1 | 1/2005 | Basser et al. |
| 2005/0068031 | A1 | 3/2005 | Frank |
| 2005/0270023 | A1 | 12/2005 | Freedman |
| 2006/0261808 | A1 | 11/2006 | Huang |
| 2010/0033182 | A1 | 2/2010 | Ozarslan et al. |
| 2010/0308821 | A1 | 12/2010 | Poupon et al. |
| 2011/0199084 | A1 | 8/2011 | Hasan |
| 2015/0115957 | A1* | 4/2015 | Topgaard ......... G01R 33/56341 324/309 |
| 2015/0130458 | A1* | 5/2015 | Topgaard ............... G01N 24/08 324/309 |

OTHER PUBLICATIONS

P.T. Callaghan, Translational dynamics & magnetic resonance, Oxford University Press, Oxford, (2011). pp. 442-445.*
Komlosh et al. "Detection of microscopic anisotropy in gray matter and in a novel tissue phantom using double Pulsed Gradient Spin Echo MR," Journal of Magnetic Resonance, Nov. 2007, vol. 189, nr. 1, p. 38-45; whole document.
Komlosh et al. "Observation in microscopic diffusion anisotropy in the spinal cord using double-pulsed gradient spin echo MRI," Magnetic Resonance in Medicine, Apr. 2008, vol. 59, nr. 4, p. 803-809; whole document.
Lawrenz et al. "A tensor model and measures of microscopic anisotropy for double-wave-vector diffusion-weighting experiments with long mixing times," Journal of Magnetic Resonance, Jan. 2010, vol. 202, nr. 1, p. 43-56; whole document.
Alexander, et al. "Diffusion Tensor Imaging of the Brian," Journal of the American Society or Experimental Neuro Therapeutics, Jul. 2007, vol. 4, nr. 3, p. 316-329, whole document.
Jespersen et al. "Determination of axonal and dendritic orientation distributions within the developing cerebral cortex by diffusion tensor imaging," IEEE Transactions on Medical Imaging, Jan. 2012, vol. 31, nr. 1, p. 16-32, whole document.
Jiang et al. "Microscopic diffusion tensor imaging of the mouse brain," NeuroImage, Apr. 2010, vol. 50, nr. 2, p. 465-474, whole document.
Arfken et al., "Mathematical Methods for Physicists", 4th edition, Academic Press, San Diego, 1995, pp. 126-129.
Bak et al., "Repulsion, A Novel Approach to Efficient 25 Powder Averaging in Solid-State NMR", Journal of Magnetic Resonance, vol. 125, pp. 132-139.
Basser et al., "Microstructural and Physiological Features of Tissues Elucidated by Quantitative-Diffusion-Tensor MRI", Journal of Magnetic Resonance, Series B, vol. 111, 1996, pp. 209-219.

Basser et al., "MR Diffusion Tensor Spectroscopy and Imaging", Biophysical Journal vol. 66, Jan. 1994, pp. 259-267.
Bax et al., "Chemical Shift Anisotropy in Powdered Solids Studied by 2D FT NMR with Flipping of the Spinning Axis", Journal of Magnetic Resonance, vol. 55, Aug. 22, 1983, pp. 494-497.
Bernin et al., "NMR Diffusion and Relaxation Correlation Methods: New Insights in Heterogeneous Materials", Current Opinion in Colloid & Interface Science, 2013, pp. 166-172.
Bihan et al., "Diffusion MRI at 25: Exploring Brain Tissue Structure and Function", Neuroimage, vol. 61, No. 2, Jun. 2012, pp. 324-341.
Callaghan et al., "Examination of the Lamellar Phase of Aerosol OT/Water Using Pulsed Field Gradient Nuclear Magnetic Resonance", J. Phys. Chem., vol. 87, 1983, pp. 1737-1744.
Duer, M., "Introduction to Solid-State NMR Spectroscopy", Blackwell Publishing Ltd, Oxford, 2004, 16 pages.
Eriksson, "Isotropic Diffusion Weighting in PGSE NMR by Magic-Angle Spinning of the q-vector", Journal of Magnetic Resonance, vol. 226, 2013, pp. 13-18.
Frydman et al., "Variable-Angle Correlation Spectroscopy in Solid-State Nuclear Magnetic Resonance", J. Chem. Phys., vol. 97, No. 7, Oct. 1992, pp. 4800-4808.
Jones et al., "Optimal Strategies for Measuring Diffusion in Anisotropic Systems by Magnetic Resonance Imaging", Magnetic Resonance in Medicine, vol. 42, 1999, pp. 515-525.
Jones et al., "White Matter Integrity, Fiber Count, and Other Fallacies: The Do's and Don'ts of Diffusion MRI", NeuroImage, 2012, 16 pages.
Jonsson et al., "Surfactants and Polymers in Aqueous Solution", John Wiley & Sons Ltd., 1998, 2 pages.
Lustig et al., "Sparse MRI: The Application of Compressed Sensing for Rapid MR Imaging", Magnetic Resonance in Medicine, vol. 58, 2007, pp. 1182-1195.
Mitchell et al., "Numerical Estimation of Relaxation and Diffusion Distributions in Two Dimensions", Progress in Nuclear Magnetic Resonance Spectroscopy, vol. 62, 2012, pp. 34-50.
Moakher, Maher, "Fourth-Order Cartesian Tensors: Old and New Facts, Notions and Applications", Q. Jl Mech. Appl. Math, vol. 61, No. 2, 2008, 23 pages.
Mobli et al., "Sparse Sampling Methods in Multidimensional NMR", Phys Chem Chem Phys., vol. 14, No. 31, Aug. 21, 2012, 16 pages.
Moseley et al., "Anisotropy in Diffusion-Weighted MRI", Magnetic Resonance in Medicine, vol. 19, 1991, pp. 321-326.
Schmidt-Rohr et al., "Multidimensional Solid-State NMR and Polymers", Academic Press, San Diego, 1994, 4 pages.
Song et al., "T1-T2 Correlation Spectra Obtained Using a Fast Two-Dimensional Laplace Inversion", Journal of Magnetic Resonance, vol. 154, 2002, pp. 261-268.
Stejskal et al., "Spin Diffusion Measurements: Spin Echoes in the Presence of a Time Dependent Field Gradient", The Journal of Chemical Physics, vol. 42, No. 288, 1965, 6 pages.
Topgaard, Daniel, "Isotropic Diffusion Weighting in PGSE NMR: Numerical Optimization of the q-MAS PGSE Sequence", Microporous and Mesoporous Materials, vol. 178, 2013, pp. 60-63.
Valette et al., "A New Sequence for Single-Shot Diffusion-Weighted NMR Spectroscopy by the Trace of the Diffusion Tensor", Magnetic Resonance in Medicine, vol. 68, 2012, pp. 1705-1712.
Vos et al., "The Influence of Complex White Matter Architecture on the Mean Diffusivity in Diffusion Tensor MRI of the Human Brain", NeuroImage, vol. 59, 2012, pp. 2208-2216.
Wedeen et al., "The Geometric Structure of the Brain Fiber Pathways", Science, vol. 335, No. 6076, Mar. 30, 2012, pp. 1628-1634.
Whittall, Kenneth P., "Analysis of Large One-Dimensional and Two-Dimensional Relaxation Data Sets", Journal of Magnetic Resonance, Series A, vol. 110, 1994, pp. 214-218.
W.S. Price, "NMR studies of translational motion," Cambridge University Press, Cambridge 2009.
P.T. Callaghan, "Translational dynamics & magnetic resonance," Oxford University Press, Oxford 2011.
Papadakis N G et al. "A study of rotationally invariant and symmetric indices of diffusion anisotropy", Magnetic Resonance Imaging, Elsevier Science, Tarrytown, NY, US, vol. 17, No. 6, Jul. 1, 1999 (Jul. 1, 1999), pp. 881-892, XP027372253, ISSN: 0730-725X [retrieved on Jul. 1, 1999].

* cited by examiner

METHOD FOR QUANTIFYING ISOTROPIC DIFFUSION AND/OR ANISOTROPIC DIFFUSION IN A SAMPLE

CROSS REFERENCE TO RELATED APPLICATIONS

This application is the National Stage Entry under 35 U.S.C. § 371 of Patent Cooperation Treaty application No. PCT/SE2015/050156, filed Feb. 10, 2015, which claims priority from U.S. Provisional Patent Application No. 61/937,941 filed Feb. 10, 2014, the contents of which are hereby incorporated by reference herein.

TECHNICAL FIELD

The present inventive concept relates to a method for quantifying isotropic diffusion and/or anisotropic diffusion in a sample.

BACKGROUND

A wide range of porous materials, from lyotropic liquid crystals [1] to brain tissue [2], contain anisotropic pores with varying sizes, shapes, and degrees of alignment on mesoscopic length scales. A complete characterization of the material requires estimation of all these parameters, but unfortunately their effects on the detected MRI (Magnetic Resonance Imaging) signal are hopelessly entangled when using conventional diffusion MRI methods based on the Stejskal-Tanner sequence [3] with two magnetic field gradient pulses. This sequence may in the following be referred to as the single pulsed field gradient (sPFG) sequence or experiment.

In diffusion MRI (dMRI), each voxel (which typically may be of a millimeter-size) of the image contains information on the micrometer-scale translational displacements of the water [15]. sPFG is used in diffusion tensor imaging (DTI), enabling quantification of mean diffusion (MD, also apparent diffusion coefficient, ADC) and diffusion anisotropy (Fractional Anisotropy, FA). Although sPFG-based DTI measures are very sensitive to changes in the cellular architecture, sPFG generally provides robust estimations only in highly organized white matter bundles. In less ordered tissue, it may provide little insight into the nature of that change, leading to common misinterpretations. For example, changes in FA are thought to represent white matter integrity, however, many factors (cell death, edema, gliosis, inflammation, change in myelination, increase in connectivity of crossing fibers, increase in extracellular or intracellular water, etc) may cause changes in FA. The limited specificity of measures such as FA and MD hinders our ability to relate the measurements to neuropathologies or to local anatomical changes such as differences in connectivity [24, 25, 26, 27]. In contrast to sPFG, non-conventional dMRI sequences can begin to bridge between the macro and micro levels of scale in the brain by providing information about distributions of cellular shapes, sizes and membrane properties within a voxel.

Building on the formal analogy between the chemical shift and diffusion anisotropy tensors, it has been shown that solid-state NMR (Nuclear Magnetic Resonance) techniques, such as "magic-angle spinning", can be adapted to diffusion MRI [4]. In its simplest form, magic-angle spinning of the q-vector allows for estimation of the distribution of isotropic diffusivities free from the confounding influence of anisotropy.

WO 2013/165312 discloses how isotropic diffusion weighting of a diffusion weighted echo signal attenuation may be achieved by a continuous or discrete modulation of the dephasing vector q(t) such that an anisotropic contribution to the echo signal is minimized, for example by employing magic-angle spinning. WO 2013/165313 discloses a method for quantifying microscopic diffusion anisotropy and/or mean diffusivity by analysis of echo attenuation curves acquired with two different gradient modulation schemes, wherein one gradient modulation scheme is based on isotropic diffusion weighting and the other gradient modulation scheme is based on non-isotropic diffusion weighting. WO 2013/165313 discloses that non-isotropic diffusion weighting may be achieved for example using single-pulse gradient spin echo (PGSE).

Although these prior art methods enable separation of isotropic and anisotropic contributions to the echo signal attenuation and quantification of inter alia microscopic fractional anisotropy, it would in some cases be desirable to have a greater freedom in terms of the gradient modulation schemes used for causing the diffusion weighting and still be able to analyze and quantify microstructure properties such as microscopic diffusion anisotropy and/or mean diffusivity e.g. for the purpose of tissue characterization using diffusion spectroscopy. For example isotropic diffusion encoding may in some cases impose high requirements on the hardware with respect to slew rate and maximum magnitude which are difficult to meet with older and less expensive equipment.

SUMMARY OF THE INVENTIVE CONCEPT

An objective of the present inventive concept is to provide a method for quantifying isotropic diffusion and/or anisotropic diffusion in a sample which does not require the use of diffusion encoding magnetic gradient pulse sequences causing isotropic diffusion encoding. Further objectives may be understood from the following summary of the inventive concept.

According to an aspect of the present inventive concept there is provided a method for quantifying isotropic diffusion and/or anisotropic diffusion in a sample, the method comprising:

performing diffusion weighted magnetic resonance measurements on the sample using diffusion encoding magnetic gradient pulse sequences $G_{i=1 \ldots m}$, wherein each magnetic gradient pulse sequence $G_i$ is generated such that a diffusion encoding tensor $b_i$ for the magnetic gradient pulse sequence $G_i$ has one to three non-zero eigenvalues, where $$b_i = \int_0^\tau q_i(t) q_i^T(t) dt,$$

$q_i(t)$ is proportional to $$\int_0^t G_i(t') dt'$$

and $\tau$ is an echo time.

The method further comprises collecting data representing magnetic resonance echo signals resulting from said measurements on the sample, wherein at least a subset of said data represents echo signals being acquired with a set of magnetic gradient pulse sequences causing anisotropic diffusion weighting, and wherein the diffusion encoding tensor for each gradient pulse sequence of said set of magnetic gradient pulse sequences has three non-zero eigenvalues, at least one of the three eigenvalues being different from the other two eigenvalues. The method further comprises calculating a degree of isotropic diffusion and/or a degree of anisotropic diffusion using said data.

The inventive method is, among others, based on the insight that performing diffusion encoding using a magnetic gradient pulse sequence (or shorter "pulse sequence") such that a diffusion encoding tensor has three non-zero eigenvalues, at least one different from the others, and causing anisotropic diffusion weighting makes it possible to control the effect of diffusion anisotropy in a sample material on the echo signal. As will be described in greater detail below, this enables accurate characterization of microscopic diffusion properties (such as isotropic and anisotropic diffusion), in particular of microscopic diffusion properties of microscopic compartments within the sample which are smaller than the spatial resolution of the magnetic resonance measurements. Moreover, such characterization is enabled while not being reliant on the use of isotropic diffusion weighting as in the prior art (which may be achieved by diffusion weighting tensors having three non-zero eigenvalues which all are equal). This may enable accurate diffusion measurements to be performed on a greater range of equipment.

According to the inventive method, each magnetic gradient pulse sequence $G_i$ is generated such that a diffusion encoding tensor $b_i$ for the magnetic gradient pulse sequence $G_i$ has 1 to 3 non-zero eigenvalues. In other words each magnetic gradient pulse sequence $G_i$ is generated such that there is a diffusion encoding tensor representation $b_i$ of the pulse sequence $G_i$ which has 1 to 3 non-zero eigenvalues. Analogously, for each magnetic gradient pulse sequence of the above-mentioned set of magnetic gradient pulse sequences causing anisotropic diffusion weighting, there is a diffusion encoding tensor representation which has 3 non-zero eigenvalues, at least one being different from the other two eigenvalues. The set of magnetic gradient pulse sequence causing anisotropic diffusion weighting may form at least a subset of the diffusion encoding magnetic gradient pulse sequences $G_{i=1\ldots m}$. The at least one eigenvalue of the diffusion encoding tensor for each of said gradient pulse sequence causing anisotropic diffusion weighting may advantageously differ by at least 5%, and even more preferably by at least 10%, from any of the other two eigenvalues. This may ensure a sufficient degree of anisotropic diffusion weighting in the sample, facilitate subsequent calculations and reduce the hardware requirements.

Said subset of data may represent echo signals acquired from a same portion of the sample, the portion including a plurality of partial volumes presenting different degrees of isotropic diffusion or different degrees and/or orientations of anisotropic diffusion, wherein the calculation of a degree of isotropic diffusion and/or a degree of anisotropic diffusion may include calculation of an estimate of a degree of isotropic diffusion and/or an estimate of a degree of anisotropic diffusion for at least one of said partial volumes.

Especially, said portion may have a spatial extension which matches a spatial resolution of the diffusion weighted magnetic resonance measurements. Hence, each one of the partial volumes may have an extension which is less than the spatial resolution. Such partial volumes may in the following be referred to as "microscopic partial volumes". Thus, in the above and in the following, the degree of isotropic diffusion and/or the degree of anisotropic diffusion calculated using said data may be referred to as a degree of isotropic diffusion and/or a degree of anisotropic diffusion for a sub-resolution or "microscopic" partial volume of the sample.

A diffusion of each partial volume may have a diffusion tensor representation D. In other words each partial volume may have a diffusion which is definable by a respective diffusion tensor D. Thus, within the portion may be represented by a distribution (for example Gaussian distribution) of diffusion tensors D.

Preferably, a plurality of diffusion weighted magnetic resonance measurements may be performed on the sample. At least two, preferably a plurality, of the diffusion encoding magnetic gradient pulse sequences $G_{i=1\ldots m}$, have tensor representations $b_i$ having one to three non-zero eigenvalues. At least two, preferably a plurality, of the diffusion encoding magnetic gradient pulse sequences are different from each other.

According to one embodiment said set of magnetic gradient pulse sequences causing anisotropic diffusion weighting forms a first set of magnetic gradient pulse sequences and said subset of data forms a first subset of data representing a first echo attenuation curve acquired with the first set of magnetic gradient pulse sequences, and wherein said data further includes at least a second subset of data representing a second echo attenuation curve acquired with a second set of magnetic gradient pulse sequences causing isotropic or anisotropic diffusion weighting. Thereby, isotropic and/or anisotropic diffusion may be quantified based on echo signals representing two different echo attenuation curves. It should be noted that the determinations "first" and "second" merely is to be construed as labels for the respective sets of magnetic gradient pulse sequences and subsets of data. They do not necessarily imply any particular ordering, i.e. that the first set of pulse sequences are applied to the sample prior to the second set of pulse sequences. Indeed, they may be applied in the reverse order or even in an arbitrary interleaved manner.

Each pulse sequence of the first set may be generated such that a first eigenvalue and a second eigenvalue of the diffusion encoding tensor for said pulse sequence are equal to each other. The third eigenvalue of a diffusion encoding tensor of the first set is different from the first and second eigenvalues (thereby causing anisotropic diffusion weighting). Moreover, each pulse sequence of the second set may be such that a first and a second eigenvalue of the diffusion encoding tensor for said pulse sequence are equal to each other. Using different magnitudes of the first and the second eigenvalues of a diffusion encoding tensor translates to varying the effect diffusion anisotropy in the sample material will have on a resulting echo signal. Hence, generating magnetic gradient pulse sequences in this manner makes it possible to probe the diffusion properties of the sample with respect to isotropy and anisotropy.

The pulse sequences of the first set and the pulse sequences of the second set of magnetic gradient pulse may have varying maximum gradient magnitudes. With respect to the diffusion weighting tensor, this may be expressed as a trace of the diffusion encoding tensor for a pulse sequence of the first (or second) set varies throughout the first (or second) set. Thereby, the strength of the diffusion weighting may be varied.

According to one embodiment, for each pulse sequence of the first set there is a first diffusion encoding tensor invariant $\Delta_{b,1}$ definable by:

$$\Delta_{b,1} = \frac{1}{b}\left(b_{zz}^{PAS} - \frac{b_{yy}^{PAS} + b_{xx}^{PAS}}{2}\right), b = b_{xx}^{PAS} + b_{yy}^{PAS} + b_{zz}^{PAS}$$

where $b_{xx}^{PAS}$ represents the first eigenvalue of the diffusion encoding tensor for said pulse sequence, $b_{yy}^{PAS}$ represents the second eigenvalue of the diffusion encoding tensor for said pulse sequence and $b_{zz}^{PAS}$ represents the third eigenvalue of the diffusion encoding tensor for said pulse sequence, and wherein the first set of pulse sequences is generated such that the first diffusion encoding tensor invariant $\Delta_{b,1}$ of the pulse sequences of the first set are equal to each other. By controlling the generation of the diffusion encoding magnetic gradient pulse sequences of the first set in this manner, the first echo attenuation curve represented by the first subset of data may represent an echo attenuation curve acquired using diffusion encoding tensors having a same degree of anisotropy $\Delta_{b,1}$.

Analogously, for each pulse sequence of the second set there may be a second diffusion encoding tensor invariant $\Delta_{b,2}$ definable by:

$$\Delta_{b,2} = \frac{1}{b}\left(b_{zz}^{PAS} - \frac{b_{yy}^{PAS} + b_{xx}^{PAS}}{2}\right), b = b_{xx}^{PAS} + b_{yy}^{PAS} + b_{zz}^{PAS}$$

where $b_{xx}^{PAS}$ represents a first eigenvalue of the diffusion encoding tensor for said pulse sequence, $b_{yy}^{PAS}$ represents the second eigenvalue of the diffusion encoding tensor for said pulse sequence and $b_{zz}^{PAS}$ represents a third eigenvalue of the diffusion encoding tensor for said pulse sequence, and wherein the second set of pulse sequences is such that the second diffusion encoding tensor invariant $\Delta_{b,2}$ of the pulse sequences of the second set are equal to each other and $\Delta_{b,2}$ is different from $\Delta_{b,1}$.

According to one embodiment calculating a degree of isotropic diffusion and/or a degree of anisotropic diffusion includes:

calculating a degree of isotropic diffusion and/or a degree of anisotropic diffusion by analyzing a change, a variation or a difference between a first echo signal acquired with a pulse sequence of the first set and a second echo signal acquired with a pulse sequence of the second set. Since the pulse sequences of the first set and the pulse sequences of the second set may be generated to present different degrees of anisotropy (i.e. $\Delta_{b,1}$ and $\Delta_{b,2}$), a change, a variation or a difference (e.g. with respect to amplitude) between the first and the second echo signals enables estimation of the degree of isotropic and/or degree of anisotropic diffusion. To simplify the estimation, the first and the second echo signals may be acquired with gradient pulses of equal maximum gradient magnitude (in other words equal values of the diffusion weighting magnitude b).

Within the scope of the inventive method, said data may, in addition to the first subset of said data and the second subset of said data, include at least a third subset of data representing a third echo attenuation curve acquired with a third set of magnetic gradient pulse sequences causing anisotropic diffusion weighting, wherein the diffusion encoding tensor for each gradient pulse sequence of the third set has 3 non-zero eigenvalues of which a first eigenvalue and a second eigenvalue are equal to each other and different from a third eigenvalue, and wherein, for each pulse sequence of the third set there is a third diffusion encoding tensor invariant $\Delta_{b,3}$ definable by:

$$\Delta_{b,3} = \frac{1}{b}\left(b_{zz}^{PAS} - \frac{b_{yy}^{PAS} + b_{xx}^{PAS}}{2}\right), b = b_{xx}^{PAS} + b_{yy}^{PAS} + b_{zz}^{PAS}$$

where $b_{xx}^{PAS}$ represents a first eigenvalue of the diffusion encoding tensor for said pulse sequence, $b_{yy}^{PAS}$ represents the second eigenvalue of the diffusion encoding tensor for said pulse sequence and $b_{zz}^{PAS}$ represents a third eigenvalue of the diffusion encoding tensor for said pulse sequence, and wherein the third set of pulse sequences is such that the third diffusion encoding tensor invariant $\Delta_{b,3}$ of the pulse sequences of the third set are equal to each other and $\Delta_{b,3}$ is different from $\Delta_{b,2}$ and $\Delta_{b,1}$. Acquiring data representing further echo attenuation curves along further "lines of constant encoding tensor anisotropy (e.g. $\Delta_{b,3}$) enables an extended probing of the diffusion properties of the sample.

According to one embodiment each pulse sequence of the first set is such that $\Delta_{b,1} > 0$, each pulse sequence of the second set is such that $\Delta_{b,2} = 0$, thereby causing isotropic diffusion weighting, and each pulse sequence of the third set is such that $\Delta_{b,3} < 0$. This enables the "shape" of the diffusion characteristics of the sample to be estimated and analyzed. In particular, it becomes possible to estimate whether the diffusion of is mainly isotropic (i.e. spherical), mainly unidirectional (i.e. oblate) or mainly planar (i.e. prolate).

According to one embodiment the method further comprises calculating, based on the data (which according to the above may include at least the first, the second and the third subset of data) representing said echo signals, a probability distribution indicating a probability of each one of said echo signals being associated with each one of a plurality of different values of a model isotropic diffusion parameter $D_{iso}$ and/or a model anisotropic diffusion parameter $\Delta_D$. This enables, among others, analysis of measurement results obtained during measurements on a sample including domains presenting different degrees of isotropic and/or anisotropic diffusion. From the probability distribution the number of such domains (i.e. components) may be identified.

The probability distribution may be calculated by determining a numerical solution to a system of equations relating the echo signals represented by said data to a product of a kernel function and said probability distribution. The system of equations may especially be a linear system of equations.

The probability distribution may be a joint probability distribution p and the kernel function may be a matrix K including at least M×N elements, each of said elements being based on an integration of $$\exp(-bD_{iso}) \cdot \exp\left(\frac{A}{3}\right) \cdot \frac{\sqrt{\pi}}{2} \frac{\gamma(1/2, A)}{\sqrt{A}},$$

where $A = 3bD_{iso}\Delta_b\Delta_D$, for a combination of values of a diffusion weighting magnitude b, a diffusion encoding tensor invariant $\Delta_b$, the model isotropic diffusion parameter $D_{iso}$ and the model anisotropic diffusion parameter $\Delta_D$. The elements of the matrix may be calculated for different combinations of values of the diffusion weighting magnitude b, the diffusion encoding tensor invariant $\Delta_b$, the model isotropic diffusion parameter $D_{iso}$ and the model anisotropic diffusion parameter $\Delta_D$.

According to one embodiment the method may further comprise:

applying each pulse sequence of said first set of magnetic gradient pulse sequences a plurality of times to the sample, with different orientations of the gradient pulse with respect to a fixed laboratory frame, and forming said first subset of data by averaging echo signal measurements acquired for the different orientations. This may be referred to as "powder averaging" whereby, in cases where there is some preferential alignment of domain orientations, it is possible to mimic the effects of random domain orientations. Such "powder averaging" may be performed also for the second set of magnetic gradient pulse sequences. Namely, by applying each pulse sequence of said second set of magnetic gradient pulse sequences a plurality of times to the sample, with different orientations of the gradient pulse with respect to a fixed laboratory frame, and forming said second subset of data by averaging echo signal measurements acquired for the different orientations.

According to one embodiment each one of said diffusion encoding magnetic gradient pulse sequences $G_i$ forms part of a (separate) triple stimulated echo sequence. This may be particularly advantageous when performing measurements on a sample including material domains with comparably short transverse relaxation time $T_2$.

According to one embodiment the method further comprises:

forming a system of equations based on an expansion of a function relating an echo signal E to a diffusion encoding tensor b and a diffusion tensor D, calculating an average diffusion tensor $<D>$ and a diffusion tensor covariance tensor $\underline{S}$ by determining a solution to the system of equations using echo signal measurements represented by said data and representations of at least a subset of the diffusion encoding tensors $b_i$, calculating an invariant bulk component $S_{bulk}$ of the covariance tensor $\underline{S}$ by projecting $\underline{S}$ onto a bulk basis $\underline{E}_{bulk}$, calculating an invariant shear component $S_{shear}$ of the covariance tensor $\underline{S}$ by projecting $\underline{S}$ onto a shear basis $\underline{E}_{shear}$, and calculating a degree of isotropic diffusion and/or a degree of anisotropic diffusion using the invariant bulk component $S_{bulk}$ and/or the invariant shear component $S_{shear}$.

This embodiment enables quantifying differences in microstructure diffusion properties, for example in terms of microscopic diffusion anisotropy, without requiring axially symmetric diffusion encoding tensors. Especially, the invariant bulk component $S_{bulk}$ may form an estimate of a variation of degrees of isotropic diffusion between the above-mentioned different partial volumes of the portion of the sample. The invariant shear component $S_{shear}$ may form an estimate of a variation of directions of anisotropic diffusion between the above-mentioned different partial volumes of the portion of the sample.

The calculated average diffusion tensor $<D>$ may be calculated for the above-mentioned portion including a plurality of partial volumes. $<D>$ may represent an estimate of an average diffusion tensor for the portion. Similarly the diffusion tensor covariance tensor $\underline{S}$ may represent an estimate of a covariance of the distribution of diffusion tensors for the portion.

The system of equations may be a linear system of equations, wherein the echo signal measurements represented by the data may be used to form constants of the linear system of equations and said at least a subset of the diffusion encoding tensors may be used to form parameters of the linear system of equations. Especially, the system of equations may be equivalent to a cumulant expansion of the function $E(b) = \langle \exp(-<b,D>) \rangle$.

The degree of anisotropic diffusion may be calculated based on a sum of the invariant shear component $S_{shear}$ and a projection of the square of the average diffusion tensor $<D>$ onto the shear basis $\underline{E}_{shear}$. Especially, the degree of anisotropic diffusion may be calculated based on a variance of said sum.

The degree of calculated anisotropic diffusion may further be based on a ratio between a projection of the square of the average diffusion tensor $<D>$ onto the bulk basis $\underline{E}_{bulk}$ and said sum. Especially, the degree of anisotropic diffusion may be calculated as an estimate of a microscopic fractional anisotropy μFA based on said ratio.

The projection of $\underline{S}$ onto the bulk basis $\underline{E}_{bulk}$, may be calculated by calculating an inner product between a matrix representation of the covariance tensor $\underline{S}$ and a matrix representation of the bulk basis $\underline{E}_{bulk}$.

The projection of $\underline{S}$ onto the shear basis $\underline{E}_{shear}$, may be calculated by calculating an inner product between the matrix representation of the covariance tensor $\underline{S}$ and a matrix representation of the shear basis $\underline{E}_{shear}$.

The projection of the square of $<D>$ onto the bulk basis $\underline{E}_{bulk}$, may be calculated by calculating an inner product between a matrix representation of the square of $<D>$ and the matrix representation of the bulk basis $\underline{E}_{Jm}$ The microscopic fractional anisotropy μFA may in particular be calculated as $$\mu FA = \sqrt{\frac{3}{2}\left(1 + \frac{<\langle D \rangle^{\otimes 2}, E_{bulk}>}{<\langle D^{\otimes 2} \rangle, E_{shear}>}\right)^{-1}}$$

where $\langle \mathbf{D}^{\otimes 2} \rangle = \underline{S} + \rangle \langle$.

The inventive method and the above-disclosed embodiments thereof may be methods for diffusion MRI, wherein the calculated degree of isotropic diffusion and/or degree of anisotropic diffusion may be used as a contrast parameter for a voxel of diffusion MRI data.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings. In the drawings like reference numerals will be used for like elements unless stated otherwise.

DETAILED DESCRIPTION OF PREFERRED EMBODIMENTS

Figure 1:
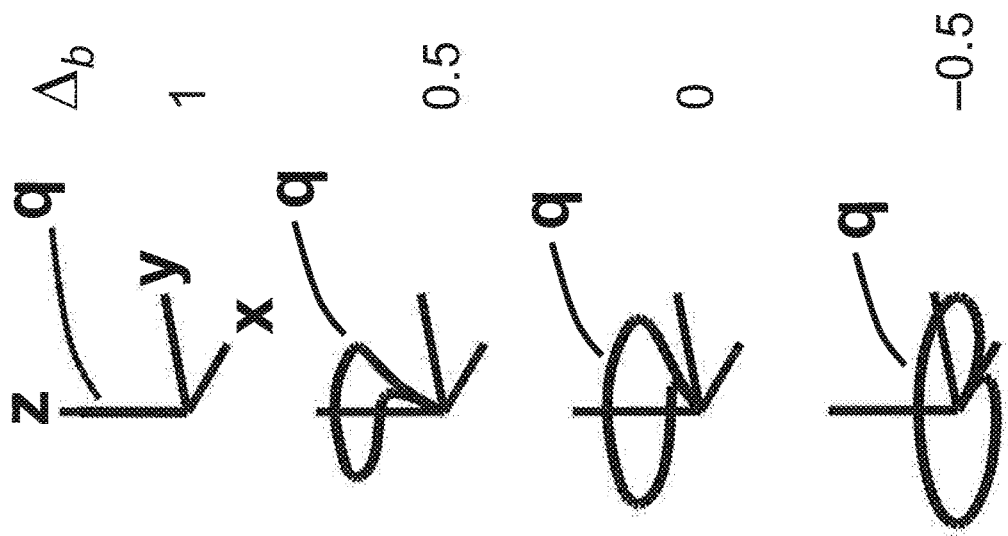
FIG. 1 illustrates some representative examples of gradient waveforms.

To facilitate understanding of the present inventive concept, a discussion of some theoretical concepts will now be provided with reference to the drawings.

Anisotropic Gaussian Diffusion

The directionality of Gaussian diffusion processes is captured in the diffusion tensor D [11]. In its principal axis system (PAS), the tensor is diagonal with the elements $D_{xx}^{PAS}$, $D_{yy}^{PAS}$, and $D_{zz}^{PAS}$. In the context of this disclosure, it is convenient to characterize the diffusion tensor with its isotropic value $D_{iso}$, anisotropy $\Delta_D$, and asymmetry $\eta_D$:

$$D_{iso} = (D_{xx}^{PAS} + D_{yy}^{PAS} + D_{zz}^{PAS})/3 \qquad (1)$$

$$\Delta_D = \frac{1}{3D_{iso}}\left(D_{zz}^{PAS} - \frac{D_{yy}^{PAS} + D_{xx}^{PAS}}{2}\right)$$

$$\eta_D = \frac{D_{yy}^{PAS} - D_{xx}^{PAS}}{2D_{iso}\Delta_D}$$

It may be noted that this formalism is reminiscent of the one used for the chemical shift tensor in solid-state NMR (e.g. as in [12] and [13]).

The elements are ordered according to the convention $|D_{zz}^{PAS} - D_{iso}| > |D_{yy}^{PAS} - D_{iso}| > |D_{xx}^{PAS} - D_{iso}|$. The numerical factors in Eq. (1) are selected to get parameters in the ranges $-1/2 \leq \Delta_D \leq 1$ and $0 \leq \eta_D < 1$. The tensor is axially symmetric when $\eta_D = 0$. Positive and negative values of $\Delta_D$ correspond to prolate and oblate tensor shapes, respectively. The convention for ordering the elements assures that the z-axis is the main axis of symmetry for both prolate and oblate tensors. It should however be noted that other conventions (e.g. using the x- or y-axis as the symmetry axis) may be used without departing from the scope of the inventive concept.

A general rotation of the PAS from the lab-frame using the Euler rotation matrices $R_z(\alpha)$, $R_y(\beta)$, and $R_z(\gamma)$ gives the following zz-element of the lab-frame diffusion tensor:

$$D_{zz}(\alpha, \beta) = \qquad (2)$$
$$D_{zz}^{PAS}\cos^2\beta + \frac{D_{yy}^{PAS} + D_{xx}^{PAS}}{2}\sin^2\beta - \frac{D_{yy}^{PAS} - D_{xx}^{PAS}}{2}\sin^2\beta\cos 2\alpha$$

Using the relations in Eq. (1), this expression can be rearranged to $$D_{zz}(\alpha, \beta) = D_{iso}[1 + \Delta_D(2P_2(\cos\beta) - \eta_D \sin^2\beta \cos 2\alpha)] \qquad (3)$$

where $P_2(x) = (3x^2 - 1)/2$ is the second Legendre polynomial. Eq. (3) reduces to $$D_{zz}(\beta) = D_{iso}[1 + 2\Delta_D P_2(\cos\beta)] \qquad (4)$$

for axially symmetric tensors, $\eta_D = 0$. As a consistency check, it may be noted that insertion of Eq. (1) into Eq. (4) gives $D_{zz}(0) = D_{zz}^{PAS}$ and $D_{zz}(\pi/2) = (D_{xx}^{PAS} + D_{yy}^{PAS})/2$ as expected.

Diffusion-Weighting Tensor b

The NMR signal is encoded with information about translational motion using a time-varying magnetic field gradient $G^T(t) = \{G_x(t), G_y(t), G_z(t)\}$. The instantaneous dephasing vector q(t) is given by the time integral $$q(t) = \gamma \int_0^t G(t')dt' \qquad (5)$$

where $\gamma$ is the magnetogyric ratio of the studied nucleus.

During a measurement, the echo signal may be recorded at the echo time $\tau$ when the spin magnetization is rephased, i.e. $q(\tau) = 0$, in other words at the time instant $t = \tau$ at which the spin magnetization is rephased. Assuming Gaussian diffusion, the signal amplitude S can be written as $$S = S_0 \exp(-b:D) \qquad (6)$$

where $S_0$ is the signal intensity at zero gradient amplitude (i.e. the non-diffusion weighted echo signal) and b:D denotes a generalized scalar product defined as $$b:D = \sum_i \sum_j b_{ij}D_{ij} \qquad (7)$$

The diffusion-weighting matrix b is given by $$b = \int_0^\tau q(t)q^T(t)dt \qquad (8)$$

In analogy with Eq. (1), the b-matrix can be characterized with the total diffusion weighting b, anisotropy $\Delta_b$, and asymmetry $\eta_b$:

$$b = b_{xx}^{PAS} + b_{yy}^{PAS} + b_{zz}^{PAS} \qquad (9)$$

$$\Delta_b = \frac{1}{b}\left(b_{zz}^{PAS} - \frac{b_{yy}^{PAS} + b_{xx}^{PAS}}{2}\right)$$

$$\eta_b = \frac{3}{2}\frac{b_{yy}^{PAS} - b_{xx}^{PAS}}{b\Delta_b}$$

It may be noted that the definition of the b-matrix through Eqs. (5) to (8) can be found in standard text books on diffusion NMR and MRI, see, e.g., chapter 4.4.1 in Price [14] or chapter 9.7.2 in Callaghan [15]. However, characterization of the b-matrix using solid-state NMR terminology is novel and, as shown below, both simplifies the notation and provides a framework for designing measurement protocols and analysis methods. The elements of the b-matrix transform under rotation according to the rules for rank-2 tensors [16]. In the following, the b-matrix (i.e. b) may hence be referred to as the b-tensor.

Variable-Angle Spinning of the q-Vector

In spherical coordinates, the q-vector may be defined by its inclination $\zeta(t)$, azimuth $\psi(t)$, and magnitude $qF(t)$, where q is the maximum magnitude and F(t) the time-dependent magnitude normalized to the interval $0 \leq F(t) \leq 1$. The Cartesian components may be obtained from the relation $$q^T(t) = \{q_x(t), q_y(t), q_z(t)\} \qquad (10)$$
$$= qF(t)\{\sin\zeta(t)\cos\psi(t), \sin\zeta(t)\sin\psi(t), \cos\zeta(t)\}$$

Insertion of Eq. (10) into Eq. (8) and application of standard trigonometric relations gives the following expressions for the b-tensor elements:

$$b_{xx} = q^2 \int_0^{t_E} F^2(t)\frac{1 - \cos^2\zeta(t) + \sin^2\zeta(t)\cos[2\psi(t)]}{2}dt \qquad (11)$$

$$b_{yy} = q^2 \int_0^{t_E} F^2(t) \frac{1 - \cos^2\zeta(t) + \sin^2\zeta(t)\cos[2\psi(t)]}{2} dt$$

$$b_{zz} = q^2 \int_0^{t_E} F^2(t) \cos^2\zeta(t) dt$$

$$b_{xy} = b_{yx} = q^2 \int_0^{t_E} F^2(t) \frac{\sin^2\zeta(t)\sin[2\psi(t)]}{2} dt$$

$$b_{xz} = b_{zx} = q^2 \int_0^{t_E} F^2(t) \frac{\sin[2\zeta(t)]\cos\psi(t)}{2} dt$$

$$b_{yz} = b_{zy} = q^2 \int_0^{t_E} F^2(t) \frac{\sin[2\zeta(t)]\sin\psi(t)}{2} dt$$

As shown in Eriksson et al. [4], all terms containing $\psi(t)$ vanish if $\zeta$ is constant and the trajectory of the q-vector has at least three-fold symmetry, i.e.

$$\psi(t) = \psi(0) + \psi\left(t + \frac{n\tau}{N}\right) + \frac{2\pi n}{N} \quad (12)$$

$$F(t) = F\left(t + \frac{n\tau}{N}\right)$$

$$N \geq 3, n = 1, 2, \ldots, N$$

Another way of nulling the terms with $\psi(t)$ in Eq. (11) is if the trajectory fulfills the condition (see reference [4])

$$\psi(t) = \psi(0) + \frac{2\pi n}{t_d} \int_0^t F(t')^2 dt' \quad (13)$$

where n is an integer other than zero and $t_d$ is an effective diffusion time given by $$t_d = \int_0^\tau F(t)^2 dt \quad (14)$$

Geometrically, this modulation of $\psi(t)$ and $F(t)$ corresponds to a q-vector spinning about the z-axis at an angular velocity $d\psi(t)/dt$ proportional to $F(t)^2$, while following a path on the surface of a cone with aperture $2\zeta$.

Explicit evaluation of the b-tensor elements in Eq. (11) gives $$b_{xx} = b_{yy} = q^2 t_d \frac{1 - \cos^2\zeta}{2} \quad (15)$$

$$b_{zz} = q^2 t_d \cos^2\zeta$$

$$b_{xy} = b_{yx} = b_{xz} = b_{zx} = b_{yz} = b_{zy} = 0$$

which upon insertion into Eq. (9) yields $$b = q^2 t_d$$

$$\Delta_b = P_2(\cos\zeta)$$

$$\eta_b = 0 \quad (16)$$

Assuming that the trajectory of the q-vector obeys Eqs. (12) or (13), the b-tensor is axially symmetric, with the z-axis as the main axis of symmetry, and has an anisotropy that can be tailored by varying the angle $\zeta$ from conventional single-directional diffusion-weighting at $\zeta=0$, via isotropic diffusion-weighting at the magic-angle $\zeta=\mathrm{acos}(1/3^{1/2})$ (i.e. using the terminology from the reference [4]), to so-called circular encoding at $\zeta=\lambda/2$ (i.e. using the terminology from the reference [17]). As long as the time-modulations of $\psi(t)$ and $F(t)$ remain the same, adjustment of $\zeta$ only affects $\Delta_b$ without influencing the values of q, $t_d$, or b.

Numerical Optimization of the Gradient Modulation Functions

For a given modulation $F(t)$ of the q-vector, its time-dependent orientation is given by the angle $\psi(t)$, obtained via the integral in Eq. (13), and the selected constant value of $\zeta$. The Cartesian components of the q-vector may be calculated with Eq. (10) and the gradient modulation functions are given by the derivative $$G(t) = \frac{1}{\gamma} \frac{dq(t)}{dt} \quad (17)$$

A conceptually simple modulation function is $F(t)=1$ in the interval $0 \leq t \leq \tau$ and $F(t)=0$ otherwise, corresponding to infinitely short and strong gradient pulses at $t=0$ and $\tau$. For practical implementation on MRI hardware with limited gradient capabilities it is necessary to have less abrupt transitions between $F(t)=0$ and 1. One possible procedure for finding optimal gradient waveforms for q-MAS diffusion weighting on clinical MRI scanners is described in [10]. In brief, $F(t)$ may be expanded as $$F(t) = \sum_{m=1}^{M} \frac{a_m}{2} \left[1 - \cos\left(\frac{2\pi m t}{\tau}\right)\right] \quad (18)$$

where the coefficients $a_m$ are optimized iteratively to get maximum diffusion weighting within the constraints of a given waveform duration $\tau$ and maximum gradient amplitude $G_{max}$ on each of the three gradient channels. The details of the optimization routine are described in the reference [10]. A final result of a joint optimization for the cone angles $\zeta=0$ and $\zeta=\pi/2$, yielding one axial and two radial gradient modulation functions that can be superposed to give q-vector modulations at arbitrary cone angles and orientations in the lab frame are listed in Table 1.

The coefficients $a_m$ in Table 1 may be referred to as coefficients for a numerically optimized q-VAS gradient waveform. Using Table 1, explicit gradient modulation functions may be obtained by selecting values of the echo time $\tau$ as well as the q-vector inclination $\zeta$ and magnitude q, and subsequently calculating the normalized q-magnitude modulation $F(t)$ with Eq. (18). The effective diffusion time $t_d$ may be calculated with Eq. (14). The q-vector azimuthal angle $\psi(t)$ may be calculated with Eq. (13). The Cartesian components of the q-vector may be calculated with Eq. (10). Finally the Cartesian components of the gradient vector may be calculated with Eq. (17).

Some representative examples of gradient waveforms are shown in FIG. 1, including the corresponding q-vector trajectories and b-tensor elements. As the azimuthal angle ψ(t) of the q-vector is varied as a function of time the modulations exemplified in FIG. 1 may be referred to as variable-angle spinning of the q-vector (q-VAS). Rows 1-4 of FIG. 1 correspond to the angles ζ=0°, 35.3°, 54.7°, and 90°, as indicated in column 1 of FIG. 1. Column 2 of FIG. 1 shows gradient modulation functions $G_x(t)$, $G_y(t)$, and $G_z(t)$ (dotted line, dashed line, and full line, respectively) obtained from the coefficients listed in Table 1. Column 3 in FIG. 1 shows corresponding q-vector modulation functions $q_x(t)$ (dotted line), $q_y(t)$ (dashed line), $q_z(t)$ (full line), and q(t) (dash-dotted line). Column 4 of FIG. 1 shows a 3D plot of the q-vector trajectory (black line) in relation to the positive x-, y-, and z-axes. As may be seen the q-vector trajectories in the second and third row lie on the surface of a cone with aperture 2ζ. The q-vector trajectory in the first row is aligned with the z-axis. The q-vector trajectory in the fourth row lies in the xy-plane. Column 5 of FIG. 1 shows the corresponding b-tensor anisotropies $\Delta_b$=1, 0.5, 0, and −0.5.

TABLE 1

| m | $a_m/10^{-3}$ |
|---|---|
| 1 | 345.5666 |
| 2 | 276.0000 |
| 3 | 186.3600 |
| 4 | 102.7100 |
| 5 | 28.8030 |
| 6 | 13.0610 |
| 7 | 3.8476 |
| 8 | 5.0764 |
| 9 | 7.8710 |
| 10 | 10.9790 |
| 11 | 7.2733 |
| 12 | 4.6788 |
| 13 | 2.0443 |
| 14 | 0.2220 |
| 15 | 1.8141 |
| 16 | 0.0001 |
| 17 | 1.0098 |
| 18 | 1.2173 |
| 19 | 0.8931 |
| 20 | 0.7950 |
| 21 | −0.2223 |

Effective Diffusion Coefficient $D_{zz}^{eff}$

Insertion of Eq. (15) into Eq. (7) gives $$b:D = q^2 t_d \left[ (D_{xx} + D_{yy}) \frac{1 - \cos^2\zeta}{2} + D_{zz}\cos^2\zeta \right] \quad (19)$$

which can be rewritten as $$b:D = b[D_{iso} + \Delta_b(D_{zz} - D_{iso})] \quad (20)$$

using the relations in Eq. (16) and the rotational invariance of the trace of the diffusion tensor $D_{iso}=(D_{xx}+D_{yy}+D_{zz})/3$. Assuming axial symmetry of the diffusion tensor, insertion of Eq. (4) yields $$b:D = bD_{iso}[1 + 2\Delta_b\Delta_D P_2(\cos\beta)] \quad (21)$$

The factors following the b-value can be interpreted as an effective diffusion coefficient $D_{zz}^{eff}(\beta)$ that depends on the anisotropy of the b-tensor as well as the orientation of the diffusion tensor in the lab frame through the angle β according to $$D_{zz}^{eff}(\beta) = D_{iso}[1 + 2\Delta_b\Delta_D P_2(\cos\beta)] \quad (22)$$

Comparing Eqs. (4) and (22) shows that the effect of the inherent diffusion anisotropy is scaled by the value of $\Delta_b$, which in turn depends on the angle between the z-axis and the spinning q-vector. The values of $D^{eff}$ are in the range between $D_{zz}^{eff}(0)=D_{iso}(1+2\Delta_b\Delta_D)$ and $D_{zz}^{eff}(\pi/2)=D_{iso}(1-\Delta_b\Delta_D)$.

Powder-Averaged Signal Attenuation and Effective Diffusivity Distribution

Consider a macroscopic sample consisting of an ensemble of randomly oriented microscopic anisotropic domains having the same values of $D_{iso}$ and $\Delta_D$. In cases where there is some preferential alignment of domain orientations, it is possible to mimic the effects random domain orientations by "powder-averaging" the data, i.e. record data for a series of directions of the symmetry axis of the q-trajectory and subsequently average the results over the various directions. In a measurement on the macroscopic sample encoded by a magnetic gradient pulse sequence represented by a q-vector having the z-axis as symmetry axis (i.e. $\eta_D$=0) each domain gives rise to a signal that may be calculated by inserting Eq. (21) into Eq. (6)

$$\frac{S(b, \Delta_b)}{S_0} = \exp\{-bD_{iso}[1 + 2\Delta_b\Delta_D P_2(\cos\beta)]\} \quad (23)$$

Integrating the contributions from all the domains gives $$\frac{S(b, \Delta_b)}{S_0} = \int_0^{\pi/2} P_\beta(\beta)\exp\{-bD_{iso}[1 + 2\Delta_b\Delta_D P_2(\cos\beta)]\}d\beta \quad (24)$$

where $P_\beta(\beta)$ is the angular distribution function, normalized in the interval 0≤β≤π/2. A random distribution of domain orientations corresponds to $P_\beta(\beta)$=sin β, which yields $$\frac{S(b, \Delta_b)}{S_0} = \exp(-bD_{iso}) \cdot \exp\left(\frac{A}{3}\right) \cdot \frac{\sqrt{\pi}}{2} \frac{\gamma(1/2, A)}{\sqrt{A}} \quad (25)$$

$$A = 3bD_{iso}\Delta_b\Delta_D$$

upon evaluation of the integral in Eq. (24). In Eq. (25), γ(s,x) is the lower incomplete gamma function. This function may for example be conveniently evaluated numerically with the "gammainc" function in Matlab. It should be noted that although the gamma and square-root factors in Eq. (25) are imaginary when the argument is negative, their ratio remains real and positive. The γ(s,x) factor could also be written in terms of the error function "erf", utilizing the fact that γ(1/2,x)∝erf($x^{1/2}$).

Figure 2:
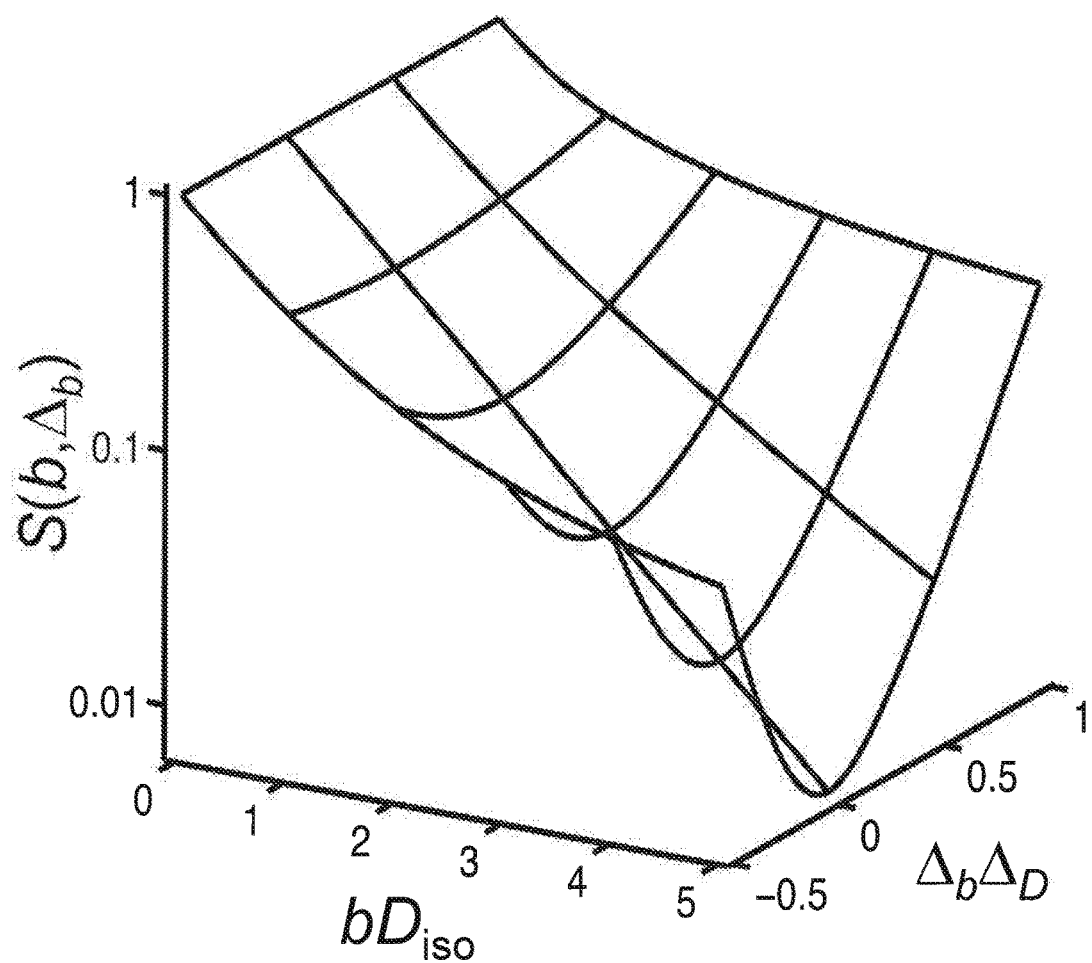
FIG. 2 illustrates a theoretical echo attenuation signal S(b, $\Delta_b$) vs. $bD_{iso}$.

FIG. 2 illustrates the theoretical signal S(b, $\Delta_b$) vs. $bD_{iso}$ according to Eq. (25), where b is the diffusion-weighting magnitude and $D_{iso}$ the isotropic diffusivity, and $\Delta_b\Delta_D$, where $\Delta_b$ and $\Delta_D$ are the anisotropies of the diffusion-weighting and diffusion tensors b and D, respectively. The surface is calculated with Eq. (25) and the parameters b, $D_{iso}$, $\Delta_b$ and $\Delta_D$ are defined from the respective tensor eigenvalues in Eqs. (1) and (9).

The expression in Eq. (25) provides a basis for analysis of experimental data. When $\Delta_b=0$, Eq. (25) reduces to a simile-exponential decay $$\frac{S(b, \Delta_b = 0)}{S_0} = \exp(-bD_{iso}) \qquad (26)$$

thus providing a simple way of extracting the isotropic part of the diffusion tensor without the confounding effects of anisotropy. When b is held constant at some finite value on the order $1/D_{iso}$, the value of $\Delta_D$ can be determined from the characteristic variation of S as a function of $\Delta_b$.

The multi-exponential signal decay in Eq. (25) can be interpreted as being the Laplace transformation of a distribution of effective diffusivities $P(D_{zz}^{eff})$ according to $$\frac{S(b)}{S_0} = \int_0^\infty P(D_{zz}^{eff})\exp(-bD_{zz}^{eff})dD_{zz}^{eff} \qquad (27)$$

where $$P(D_{zz}^{eff}) = \frac{1}{2\sqrt{3D_{iso}\Delta_b\Delta_D[D_{zz}^{eff} - D_{iso}(1 - \Delta_b\Delta_D)]}} \qquad (28)$$

in the range of $D_{zz}^{eff}$ from $D_{iso}(1-\Delta_b\Delta_D)$ to $D_{iso}(1+2\Delta_b\Delta_D)$ and $P(D_{zz}^{eff})=0$ otherwise. The distribution has a singularity at $D_{zz}^{eff}=D_{iso}(1-\Delta_b\Delta_D)$, corresponding to the domain orientation $\beta=\pi/2$. Eq. (28) is analogous to the "powder-pattern" NMR spectrum obtained for an axially symmetric chemical shift anisotropy tensor. The mean value of the distribution is $D_{iso}$, while the $2^{nd}$ and $3^{rd}$ central moments, $\mu_2$ and $\mu_3$, are $$\mu_2 = 4/5(D_{iso}\Delta_b\Delta_D)^2 \qquad (29)$$

and $$\mu_3 = 16/35(D_{iso}\Delta_b\Delta_D)^3 \qquad (30)$$

respectively.

Signal Intensity for a Multi-Domain Material

A material consisting of a collection of domains with different values of $D_{iso}$ and $\Delta_D$ gives rise to a powder-averaged signal that can be expressed as the integral transform $$\frac{S(b, \Delta_b)}{S_0} = \int_{-1/2}^{1}\int_0^\infty K(b, \Delta_b, D_{iso}, \Delta_D)P(D_{iso}, \Delta_D)dD_{iso}d\Delta_D \qquad (31)$$

where $P(D_{iso},\Delta_D)$ is the 2D joint probability distribution of $D_{iso}$ and $\Delta_D$. The kernel $K(b,\Delta_b,D_{iso},\Delta_D)$ is given by the right-hand side of Eq. (25) and maps the 2D "analysis-space" $(D_{iso},\Delta_D)$ onto the 2D "acquisition-space" $(b,\Delta_b)$. Estimating $P(D_{iso},\Delta_D)$ from an experimental set of data $I(b,\Delta_b)$ may be considered as an ill-posed problem and may benefit from special procedures to ensure numerically stability. Based on the approaches used for tackling similar problems in NMR diffusion and relaxation correlation methods [18-20], with some additional inspiration from compressed sensing [8, 9], the procedure outlined below may be used.

Eq. (31) can be discretized and written in matrix form as $$s = Kp \qquad (32)$$

where s is a column vector of signal amplitudes measured for a M combinations of $(b,\Delta_b)$, p is the sought-for column vector of probabilities for N discrete pairs of $(D_{iso},\Delta_D)$, and K is the matrix version of the kernel $K(b,\Delta_b,D_{iso},\Delta_D)$ calculated for an M×N grid of $(b,\Delta_b)$ and $(D_{iso},\Delta_D)$ pairs. Eq. (32) is a set of linear equations and can in principle be solved by straight-forward matrix inversion if the problem is over-determined, i.e M>N. Unfortunately, the "smoothness" of the kernel renders this direct approach extremely sensitive to experimental noise, with wild fluctuations of the solution vector p for minor changes in the input data vector s. Assuming that the material consists of a few discrete components, it may be advantageous to look for a solution that is sparse, meaning that most of the elements of p are zero.

Based on the considerations above, a sparse solution p that is consistent with experimental data s may be estimated by minimizing the function $$f(p) = \sum_{i=1}^N \sum_{j=1}^J |K_{ij}p_j - s_i|^2 + \lambda\sum_{j=1}^M |p_j| \qquad (33)$$

where the $1^{st}$ term is the least-squares misfit and the $2^{nd}$ term is the $l_1$-norm weighted by the regularization parameter $\lambda$. Combined with non-negativity constraint on the elements of p, Eq. (33) can be formulated as a quadratic programming problem $$f(p) = p^T K^T Kp - 2s^T Kp + s^T s + \lambda 1^T p \qquad (34)$$

which is readily solved by, e.g., the "quadprog" function in the optimization toolbox of Matlab.

Example Experiments

In the present and the subsequent section, a number of examples of proof-of-principle experiments will be described as well as results thereof. According to these examples, experiments were carried out on lyotropic liquid crystals with the detergent Aerosol-OT and water consisting of an equimolar mixture of $H_2O$ and $D_2O$. Based on the equilibrium phase diagram (see e.g. reference [21]), the detergent concentration was chosen to give three different liquid crystalline phases: lamellar (25 and 75 wt %), bicontinuous cubic (80 wt %), and reverse hexagonal (85 wt %). The samples were initially weighed into 10 mL vials, allowing for thorough mixing, and subsequently 400 μL was transferred to 5 mm disposable NMR tubes. The phase symmetry was independently verified by recording small-angle x-ray scattering patterns and $^2$H NMR spectra. A sample with two distinct diffusion tensor components was prepared by inserting the 5 mm NMR tube with the 25 wt % Aerosol-OT sample into a 10 mm NMR tube with decanol.

Diffusion magnetic resonance experiments were performed on a Bruker Avance-II 500 MHz spectrometer with an 11.7 T magnet equipped with a Bruker MIC-5 microimaging probe giving maximum magnetic field gradients of 3 T/m in three orthogonal directions. The q-VAS gradient modulation was implemented by including the waveforms shown in FIG. 1 on both sides of the 180° RF pulse in a standard $^1$H spin echo pulse sequence. The signal recorded during the second half of the spin echo yields a high-resolution spectrum after Fourier transformation, thus permitting the separation of the water $^1$H signal from the ones originating from the detergent. For studies of systems with short transverse relaxation time $T_2$, it is advantageous to implement the variation of the diffusion-weighting anisotropy $\Delta_b$ by adjusting the directions of the pulsed field gradients in a triple-stimulated echo sequence. The three gradient directions have the azimuth angle $\psi=0°$, 120°, and 240° and the inclination $\zeta$, which gives $\Delta_b$ through Eq. (16).

The 75, 80, and 85 wt % Aerosol-OT/water samples were investigated with the triple-stimulated echo implementation using three pairs of gradient pulses with duration $\delta=1$ ms and leading-edge separation $\Delta=100$ ms. A rectangular grid of the acquisition space (b,$\Delta_b$) was sampled by varying the amplitude of the gradient pulses and the angle $\zeta$. The maximum gradient amplitude was on the order of 1 T/m and adjusted for the different samples to get approximately the same maximum signal attenuation. Both the cubic and reverse hexagonal samples give sufficiently narrow Aerosol-OT resonance lines to be detectable with the triple-stimulated sequence. Empirically, it was found that the water and Aerosol-OT resonance lines overlap at 25° C., but that the overlap is rendered insignificant by increasing the temperature to 80° C. For consistency, the 75, 80, and 85 wt % samples were all studied at 80° C. The samples remain in the same liquid crystalline phase as at 25° C. according to the equilibrium phase diagram and confirmed by $^2$H spectroscopy measurements.

The 25 wt % Aerosol-OT/water/decanol sample was studied at 25° C. with the spin echo version at a gradient modulation duration $\tau=140$ ms and maximum gradient amplitude 0.090 T/m. The (b,$\Delta_b$)-space was sampled in a zig-zag pattern by varying the maximum gradient amplitude and $\zeta$. Although the resonance lines could be separated by Fourier transformation, they were recorded jointly to give a signal containing multiple components with different diffusion behavior. In practice, only water and the terminal methyl group of the decanol have sufficiently long $T_2$ to survive the lengthy spin echo sequence.

In order to assure that the data corresponds to a random distribution of domain orientations, as required by Eq. (25), the acquisition was repeated and averaged for 31 different "cone orientations", i.e. orientations of the main symmetry axis of the q-vector trajectory. These directions were chosen according to the electrostatic repulsion scheme (see reference [22] and [23]).

Results of the Example Experiments

Figure 3:
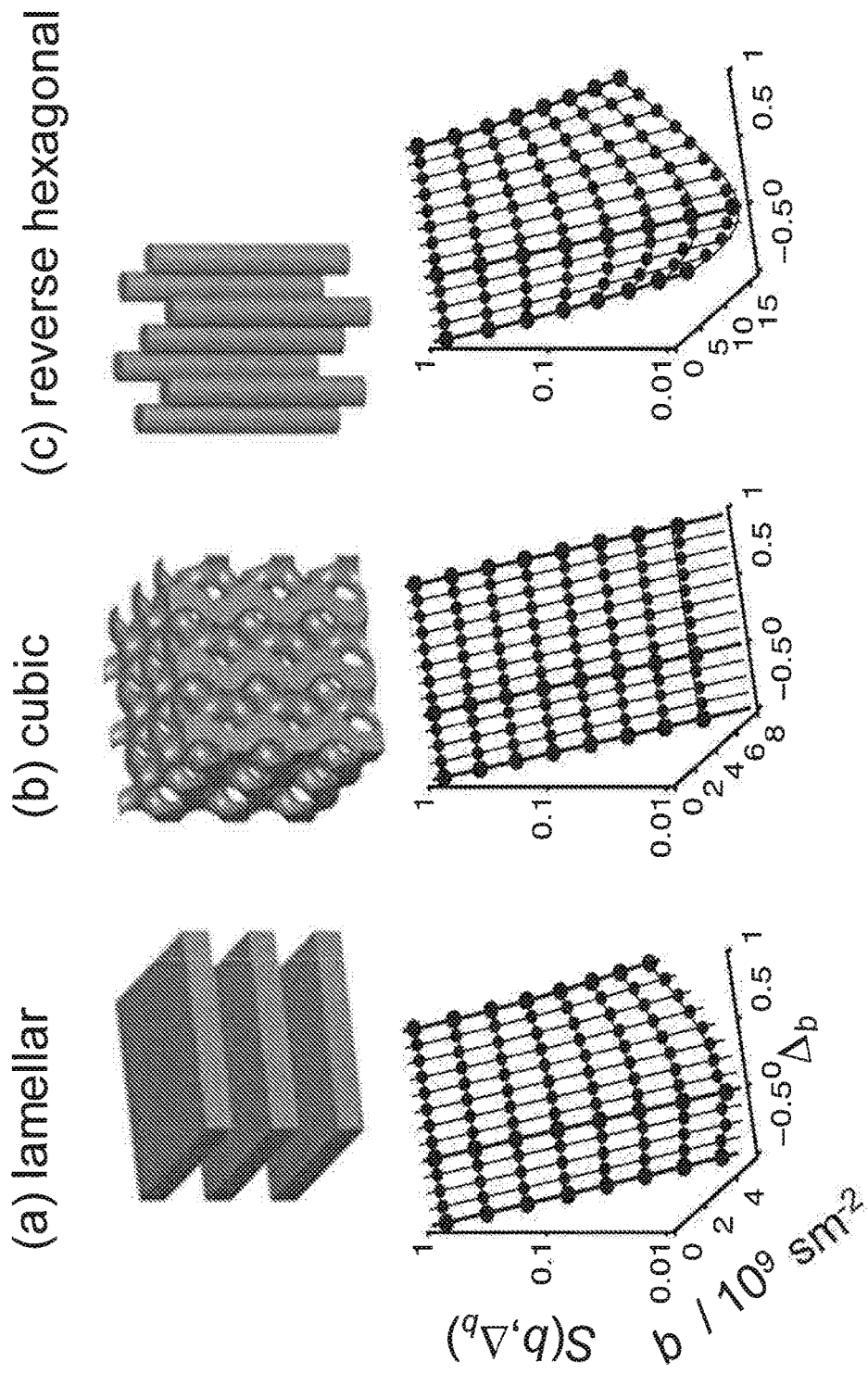
FIGS. 3-4 illustrate a number of experimental results.

FIG. 3 shows experimental data for lamellar, bicontinuous cubic, and reverse hexagonal liquid crystalline phases. The data was fitted with Eq. (25), yielding values of the diffusion anisotropy $\Delta_D$ consistent with the known microstructure. It is noteworthy that the sign of $\Delta_D$ can be extracted from the characteristic variation of the signal as a function of $\Delta_b$ as long as $bD_{iso}$ is on the order of unity and above.

In more detail, FIG. 3 shows data representing the measured signal attenuations S(b, $\Delta_b$) vs. the diffusion-weighting magnitude b and anisotropy $\Delta_b$ for AOT/water liquid crystals of the (a) lamellar, (b) bicontinuous cubic, and (c) reverse hexagonal types. The top row shows schematic illustrations of these types. These geometries characterize the respective water compartment geometries on the length scale of tens of nanometers. The filled circles represent experimental data points sampled on a rectangular grid in the (b,$\Delta_b$)-space. The grid illustrates a fit of Eq. (25) to the experimental data using the initial signal intensity $S_0$, the isotropic diffusivity $D_{iso}$, and the diffusion anisotropy $\Delta_D$ as adjustable parameters. The fit yields $D_{iso}/10^{-9}$ m$^2$s$^{-1}$=3.53 (lamellar), 2.37 (cubic), and 1.22 (reverse hexagonal), as well as $\Delta_D$=−0.38 (lamellar), 0.00 (cubic), and 0.80 (reverse hexagonal).

Figure 4:
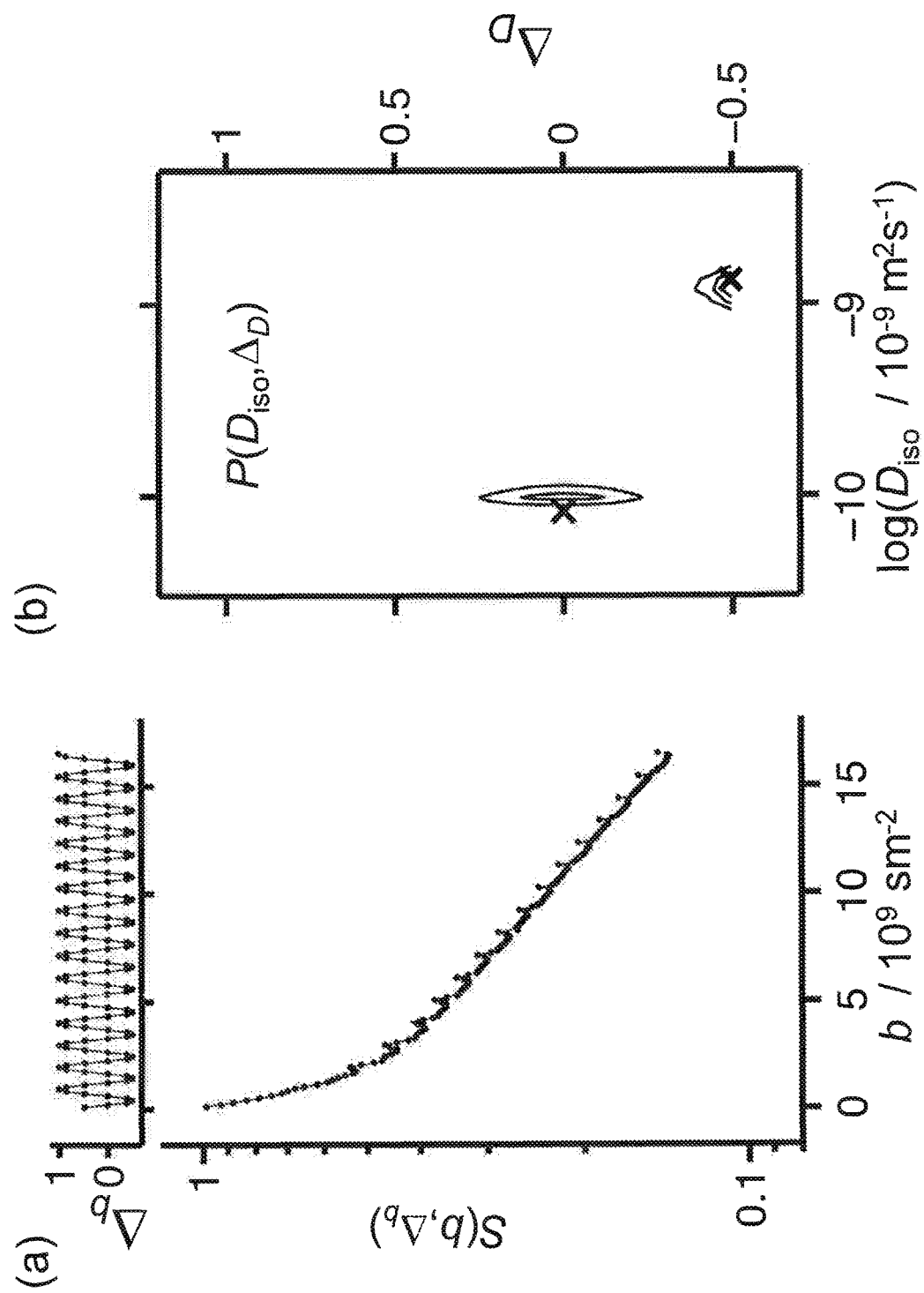

The results for the liquid crystal/decanol sample are indicated in FIG. 4. The zig-zag sampling of the (b,$\Delta_b$)-space facilitates display of the data in a 2D plot with signal vs. b. In such a plot, the presence of multiple components with different $D_{iso}$ can be discerned as curvature in the lower envelope of the data, while non-zeros values of $\Delta_D$ result in oscillations at a frequency given by the sampling pattern. The amplitude of the oscillations is related to the magnitude of $\Delta_D$, while the ratio between the local maxima corresponding to $\Delta_b$=1 and −0.5 gives the sign of $\Delta_D$.

The S(b,$\Delta_b$) data is converted to a probability distribution $P(D_{iso},\Delta_D)$ through the $l_1$-regularized model-free approach as described above. The resulting distribution contains components at ($D_{iso}=10^{-10}$ m$^2$/s, $\Delta_D$=0) and ($D_{iso}=10^{-9}$ m$^2$/s, $\Delta_D$=−0.5), corresponding to decanol and water, respectively. Once it is known that the distribution contains two components, the coordinates and amplitudes of these are more accurately determined by a two-component model fit where the signal from each of the components is described by Eq. (25). The result of such a fit is also shown in FIG. 4b. The obtained results are consistent with the known isotropic diffusion of decanol and the lamellar symmetry of the liquid crystalline phase. In more detail FIG. 4a illustrates the experimental water and decanol signal S(b, $\Delta_b$) vs. the diffusion-weighting magnitude b for a tube-in-tube sample with an AOT/water lamellar liquid crystal (inner tube) and decanol (outer tube). The zig-zag sampling pattern of the (b,$\Delta_b$)-space is shown on top. FIG. 4b shows the probability density $P(D_{iso},\Delta_D)$ consistent with the S(b, $\Delta_b$) data. The contour lines show the result of a $l_1$-regularized model-free estimate, while the crosses indicate the results of a two-component model fit giving $D_{iso}/10^{-9}$ m$^2$s$^{-1}$=0.083 (decanol) and 1.33 (water), as well as $\Delta_D$=0.00 (decanol) and −0.496 (water). The points in FIG. 4a indicate the experimental data while the black line represents the two-component model fit.

Description of Embodiments

In accordance with the present inventive concept there is provided a method for quantifying isotropic diffusion and/or anisotropic diffusion in a sample. With reference to the preceding description, the isotropic diffusion may for example be quantified by the isotropic value $D_{iso}$ for a diffusion tensor D (as defined in connection with Eq. 1 above). The anisotropic diffusion may for example be quantified by the anisotropy $\Delta_D$ for the diffusion tensor D.

The various calculation performed in the method may for example be implemented using a set of software instructions which may be stored on or embodied on a non-transitory computer storage medium.

The method may be performed using a state-of-the-art NMR spectrometer or MRI device. As is well-known in the art, such devices may include one or more processors for controlling the operation of the device, inter alia the generation of the magnetic gradient pulse sequences, the acquisition of echo signals as well as sampling and digitizing the measured signals for forming data representing the acquired echo signals. The generation of the diffusion encoding magnetic gradient pulse sequences may be implemented using software instructions which may be stored on a computer readable media (e.g. on a non-transitory computer readable storage medium) and be executed by the one or more processors of the device. The software instructions may for example be stored in a program/control section of a memory of the device, to which the one or more processors of the device has access. Collected data representing the measurements may be stored in a data memory of the device, or of a computer or the like which may be connected to the device. The calculations of the method may be implemented software instructions which may be stored on a computer readable media and be executed by the one or more processors of the device. However it is equally possible to carry out the calculations on a device which is separate from the NMR spectrometer or MRI device, for example on a computer. The device and the computer may for example be arranged to communicate via a communication network such as a LAN/WLAN or via some other serial or parallel communication interface. It should further be noted that, instead of using software instructions, the operation of the method may be implemented in dedicated circuitry of the device such in one or more integrated circuits, in one or more application-specific integrated circuits (ASICs) or field-programmable gate arrays (FPGAs), to name a few examples.

The method comprises performing diffusion weighted magnetic resonance measurements on the sample using diffusion encoding magnetic gradient pulse sequences which may be denoted $G_{i=1 \ldots m}$. With reference to the preceding description, each magnetic gradient pulse sequence $G_i$ is definable by, or has a representation in the form of, a diffusion encoding tensor $b_i$ having three non-zero eigenvalues, where $$b_i = \int_0^\tau q_i(t) q_i^T(t) dt \qquad \text{(Equation (5))}$$

and $q_i(t)$ is the dephasing vector which is proportional to $$\int_0^t G_i(t') dt'. \qquad \text{(Equation (8))}$$

For the purpose of acquiring echo signals, each diffusion encoding magnetic gradient pulse sequences may be supplemented with one or imaging magnetic gradients and optionally magnetic gradient correction gradients, as is well-known in the art. Hence each diffusion weighted magnetic resonance measurement may be performed using a magnetic pulse gradient sequence including the diffusion encoding magnetic gradient pulse sequence Gi, an imaging magnetic gradient sequence and optionally a correction magnetic gradient sequence. In some cases these sequences may overlap in time. However, even in such a case at least a part of the sequence may be described or represented by a diffusion encoding tensor $b_i$ having the above-mentioned properties.

The method further comprises collecting data representing the echo signal measurements. The data collection may include sampling and digitizing an echo signal received from the portion of interest of the sample. In line with the above, each echo attenuation measurement may be in the form of a echo signal amplitude $S_i$ which, assuming Gaussian diffusion, has a dependence on the diffusion encoding tensor $b_i$ and D as given by Eq. (6). The measurements may be spin echo measurements or stimulated echo measurements, for example triple stimulated echo measurements.

The portion may as discussed above include a plurality of "microscopic" partial volumes presenting different degrees of isotropic diffusion (e.g. Diso as defined above) or different degrees and/or orientations of anisotropic diffusion (e.g. $\Delta_D$ as defined above). As is well-known in the art the spatial resolution of an NMR spectrometer or MRI device is limited by inter alia the strength of the magnetic field, the magnitude of the gradient pulse sequence applied to the sample and slew rate. The data analysis disclosed in the below enables estimation of diffusion properties of the microscopic partial volumes within the portion, i.e. beyond the traditional resolution limitations of the measurements. To identify the echo signal component corresponding to the portion, the measurement signals from the sample may be subjected to a Fast Fourier Transform as is well-known in the art, thereby transforming the spectral components of each echo signal from the sample into a plurality of spatial regions of the sample.

According to the inventive method, at least a subset of the data representing the echo signal measurements is acquired with a set of magnetic gradient pulse sequences causing anisotropic diffusion weighting, wherein the diffusion encoding tensor for each gradient pulse sequence of the set of magnetic gradient pulse sequences has 3 non-zero eigenvalues, at least one of the 3 eigenvalues being different from the other eigenvalues. With reference to Eq. (9) the 3 non-zero eigenvalues of each pulse sequence may be denoted $b_{xx}^{PAS}$, $b_{yy}^{PAS}$ and $b_{zz}^{PAS}$. Analogously, each pulse sequence of said set is definable by a total diffusion weighting b, an anisotropy $\Delta_b$, and an asymmetry $\eta_b$, following the definitions in Eq. (9). These parameters form invariant parameters for each pulse sequence. The parameter b represents the diffusion weighting magnitude for the gradient sequence.

An embodiment will now be described wherein echo signals are acquired using magnetic gradient pulse sequences $G_{i=1 \ldots m}$ generated such that the asymmetry parameter $\eta_b$ equals 0. This implies that at least two of the eigenvalues of the corresponding diffusion weighting encoding tensor are equal (i.e. $b_{xx}^{PAS}=b_{yy}^{PAS}$). Data representing the echo signal measurements may be collected as described above. The data may include a number of distinct subsets of data, each acquired using a different set of pulse sequences. For example, the data may include a first subset of data, a second subset of data and a third subset of data. The first, second and third subset of data may represent echo signal measurements acquired using a first (denoted $G_{i=1 \ldots j}$), a second (denoted $G_{i=j+1 \ldots k}$) and a third set (denoted $G_{i=k+1 \ldots m}$) of magnetic gradient pulse sequences, respectively. Although reference is made to these three subsets of data and sets of pulse sequences, the method is applicable also to both greater and smaller numbers of such subsets of data and sets of pulse sequences.

The first set of pulse sequences may each be generated to have an equal degree of anisotropy $\Delta_{b,1}$ but different maximum amplitudes b (defined in accordance with Eq. (9) and (16)). Analogously, the second set of pulse sequences may each be generated to have an equal degree of anisotropy $\Delta_{b,2}$ but different maximum amplitudes b. Likewise, the third set of pulse sequences may each be generated to have an equal degree of anisotropy $\Delta_{b,3}$ but different maximum amplitudes b. For example, the pulse sequences may be generated using the approach described in connection with Table 1. With reference to FIG. 2, it may be understood that the first, the second and the third subsets of data each represent respective echo attenuation curves acquired along respective lines of constant anisotropy, namely $\Delta_{b,1}$, $\Delta_{b,2}$ and $\Delta_{b,3}$. Using the thusly collected data, $D_{iso}$ for the diffusion tensor D and/or $\Delta_D$ for the diffusion tensor D may be calculated.

For a sample including an ensemble of randomly oriented microscopic partial volumes of generally similar degrees of anisotropic and isotropic diffusion, (estimates of) $D_{iso}$ and $\Delta_D$ for a randomly oriented diffusion tensor D characterizing diffusion in each partial volume, may be calculated by fitting the data using Eq. (25). If for example the second subset of data is acquired with $\Delta_b^2=0$ the isotropic value $D_{iso}$ for the diffusion tensor D may be directly calculated using Eq. 26 and the second subset of data.

In case there is some preferential alignment of the orientations of diffusion in the partial volumes in the sample, powder averaging may be applied, wherein each pulse sequence of each one of the first, second and third sets of magnetic gradient pulse sequences may be applied a plurality of times to the sample, with different orientations of the gradient pulse with respect to a fixed laboratory frame. The first, second and third subsets of data may thereafter be formed by averaging echo signal measurements acquired for the different orientations. Equations (25) and (26) may thereafter be used in a same manner as for a sample including randomly oriented domains.

For a sample including a collection of microscopic partial volumes exhibiting different degrees of anisotropic and/or isotropic diffusion (i.e. two- or multi-component material), the data (with or without powder averaging depending on whether there is a preferential alignment of orientations or not) may be used to estimate $D_{iso}$ and/or the $\Delta$ for each component. In particular, the data analysis approach described in connection with Eqs. (32-34) may be used. The kernel matrix may be calculated using pairs of the model parameters $(b,\Delta_b)$ and the model parameters $(D_{iso},\Delta_D)$, where the values of $(b,\Delta_b)$ correspond to the values for each gradient pulse sequence used during the measurements, and the values of $(D_{iso},\Delta_D)$ are selected to cover the region of interest for the sample, for example based on a priori knowledge of the range of possible values of $(D_{iso},\Delta_D)$ for the particular sample. If used in connection with diffusion MRI, $D_{iso}$ and/or the $\Delta_D$ may be used to generate contrast for a voxel representing the portion of the sample. Similar calculations may be performed to generate contrast for voxels representing other portions of the sample.

Although in the above, calculation of $D_{iso}$ and $\Delta_D$ is described employing e.g. Eqs. (25-26) it should be noted that the parameters may be calculated or estimated also in other ways. The measurement data could also be fitted using a different model function relating diffusion weighted signals to the relevant diffusion metrics, e.g. $D_{iso}$ or $\Delta_D$. As one example of an alternative to Eq. (25), an expansion of Eq. (25) in terms of moments $\mu_2$, $\mu_3$, etc. of the distribution of diffusivities could be used instead. Another example would be to approximate the distribution of diffusivities by the gamma distribution function.

In the above, various embodiments have been disclosed wherein diffusion parameters are calculated based on echo signal measurements acquired using diffusion encoding tensors being axially symmetric. In the following, embodiments of the inventive method will be disclosed which do not require axially symmetric diffusion encoding tensors. One objective is to provide methods that can quantify differences in microstructure, for example in terms of microscopic diffusion anisotropy on the basis of diffusion properties of "microscopic" partial volumes of a portion of the sample. To facilitate understanding of the following embodiments, a discussion of some theoretical concepts will now be provided.

Theory

Consider a portion of a sample (on which diffusion NMR/MRI is to be performed) which includes a collection of partial volumes (e.g. "microscopic" partial volumes), where in each partial volume the diffusion is Gaussian and described by the diffusion tensor D. Diffusion properties in these microenvironments within the portion may be modeled with a Gaussian distribution over tensors. The tensor D may thus be referred to as a stochastic variable with expectation $\langle D \rangle$, where $\langle \bullet \rangle$ represents integration over the distribution in the portion. The covariance of D may then be given by a 4th-order tensor $\underline{S}$ defined using a standard definition of covariance according to $$\underline{S} = \langle \mathbf{D}^{\otimes 2} \rangle - \rangle \tag{35}$$

where $\mathbf{D}^{\otimes 2} = D \otimes D$ is a fourth-order tensor obtained from the outer product of D with itself. The diffusion encoded MR-signal E from a portion including multiple such microscopic partial volumes, each having Gaussian diffusion, may be estimated by $$E(b) = \langle \exp(-\langle b, D \rangle) \rangle, \tag{36}$$

where $\langle \bullet, \bullet \rangle$ is the inner product. To facilitate understanding it may be noted that equation (36) is based on equation (6) however differs in that E denotes the normalized echo signal intensity (i.e. $S/S_0$) and includes the signal contribution from each of the microscopic environments of the portion.

Furthermore, to simplify notation in the following the inner product will be used instead of the generalized scalar product used in Eq. (7). From a cumulant expansion of equation (36) follows that, $$E(b) \approx \exp\left(-\langle b, \langle D \rangle \rangle + \frac{1}{2} \langle B, \underline{S} \rangle\right) \tag{37}$$

where $\underline{B} = \mathbf{b}^{\otimes 2}$ and $\underline{S}$ is the covariance of tensors within the portion (which in the case of diffusion MRI is represented by a voxel). To facilitate understanding, a detailed derivation of the cumulant expansion is provided below.

The approximation in Eq. 37 is a cumulant expansion where $e(b)=\log E(b)$ is expanded around $b=0$ (where b corresponds to the total diffusion weighting in analogy with Eq. 9) according to $$e(b) = \log\langle \exp(-b \langle N, D \rangle) \rangle \approx f(0) + bf'(0) + \frac{1}{2}b^2 f''(0) \tag{38}$$

where $$f'(b) = \frac{E'(b)}{E(b)} \tag{39}$$

$$f''(b) = \frac{E''(b)}{E(b)} - \left(\frac{E'(b)}{E(b)}\right)^2 \tag{40}$$

For $b=0$, these functions evaluates to $$E(0)=1 \tag{41}$$

$$E'(0) = -\langle \langle N,D \rangle \rangle = -\langle N, \langle D \rangle \rangle \tag{42}$$

$$E''(0) = \langle \langle N,D \rangle^2 \rangle = \langle \underline{N}, \underline{D} \rangle \rangle = \langle \underline{N}, \langle \underline{D} \rangle \rangle \tag{43}$$

where $\underline{D} = \mathbf{D}^{\otimes 2}$. Hence $f''(0) = \langle \underline{N}, \langle \mathbf{D}^{\otimes 2} \rangle - \langle \mathbf{D} \rangle^{\otimes 2} \rangle = \langle \underline{N}, \underline{S} \rangle$.

In case of the diffusion tensor D, two common invariant representations are the mean diffusivity (MD) and the fractional anisotropy (FA). MD may be calculated as a projection onto an isotropic base $E_{iso}$, according to $$MD(D) = \langle D, E_{iso} \rangle, \tag{44}$$

where $E_{iso}=3I$, i.e., a third of the identity tensor. This is equivalent to the parameter $D_{iso}$ defined in connection with Equation (1). Analogously the fourth order covariance tensor $\underline{S}$ may be projected onto an isotropic base to obtain a rotationally invariant parameter. The isotropic 4th-order tensor $\underline{S}$, however, has two isotropic components, which in analogy with the field of mechanics may be interpreted as bulk and shear modulus of the 4th-order stress tensor (see e.g. reference [28]). These two bases may be defined by $$\underline{E}_{bulk} = \mathbf{E}_{iso}^{\otimes 2} \tag{45}$$

and $$\underline{E}_{shear} = 1/3\underline{I} - \mathbf{E}_{iso}^{\otimes 2} \tag{46}$$

where $\underline{I}$ is the identity tensor. Note that $\underline{E}_1 = \underline{E}_{bulk}$ and $\underline{E}_2 = \underline{E}_{shear}$ are orthogonal, i.e., $$\langle \underline{E}_i, \underline{E}_j \rangle = \delta_{ij}. \tag{47}$$

where $\delta_{ij}$ is unity if i=j, and zero otherwise.

Similarly to estimating the mean diffusivity MD as in Eq. (44), the 4th-order covariance tensor may be projected onto its two isotropic basis elements. Projecting onto $\underline{E}_{bulk}$ yields the variance in mean diffusivities $V_{MD}$ (which also may be denoted $S_{bulk}$) according to, $$\langle \underline{S}, \underline{E}_{bulk} \rangle = \langle MD(D)^2 \rangle - MD(\langle D \rangle)^2 = V_{MD}.$$

This follows from the following equations Eqs. (49-53):

$$\langle \underline{S}, \underline{E}_{bulk} \rangle = \langle \langle D^{\otimes 2} \rangle - \langle D \rangle^{\otimes 2}, E_{iso}^{\otimes 2} \rangle = \tag{49}$$

$$= \langle \langle D^{\otimes 2} \rangle, E_{iso}^{\otimes 2} \rangle - \langle \langle D \rangle^{\otimes 2}, E_{iso}^{\otimes 2} \rangle = \tag{50}$$

$$= \langle \langle D^{\otimes 2}, E_{iso}^{\otimes 2} \rangle \rangle - \langle \langle D \rangle, E_{iso} \rangle^2 = \tag{51}$$

$$= \langle \langle D, E_{iso} \rangle^2 \rangle - \langle \langle D, E_{iso} \rangle \rangle^2 = \tag{52}$$

$$= \langle MD^2 \rangle - \langle MD \rangle^2 = V_{MD} \tag{53}$$

Projecting $\underline{S}$ onto $\underline{E}_{shear}$ yields another invariant parameter related to the variance of tensor eigenvalues, $$\langle \underline{S}, \underline{E}_{shear} \rangle = \langle V_\lambda(D) \rangle - V_\lambda(\langle D \rangle) = \Delta V_\lambda, \tag{54}$$

(which also may be denoted $S_{shear}$) where $V_\lambda(\bullet)$ yields the variance of diffusion tensor eigenvalues ($\lambda_i$, i=1, 2, 3), $$V_\lambda(D) = \langle D^{\otimes 2}, E_{shear} \rangle = \tag{55}$$

$$= \frac{1}{3}\sum_{i=1}^{3} \lambda_i^2 - \frac{1}{3}\left(\sum_{i=1}^{3} \lambda_i\right)^2. \tag{56}$$

This follows from following equations Eqs. (57-64): Considering the projection not of $\underline{S}$ but of $\mathbf{D}^{\otimes 2}$ on $\underline{E}_{shear}$, $$\langle D^{\otimes 2}, \underline{E}_{shear} \rangle = \langle D^{\otimes 2}, \frac{1}{3}I - E_{iso}^{\otimes 2} \rangle \tag{57}$$

$$= \langle D^{\otimes 2}, \frac{1}{3}I \rangle - \langle D^{\otimes 2}, E_{iso}^{\otimes 2} \rangle = \tag{58}$$

$$= \langle D^2, E_{iso} \rangle - \langle D, E_{iso} \rangle^2 = \tag{59}$$

$$= \frac{1}{3}\sum_{i=1}^{3} \lambda_i^2 - \left(\frac{1}{3}\sum_{i=1}^{3}\lambda_i\right)^2 = V_\lambda(D) \tag{60}$$

where the following relationship was utilized:

$$\langle D^2, E_{iso} \rangle = 1/2 Tr(DD) = 1/3 \langle D, D \rangle = \langle \mathbf{D}^{\otimes 2}, 1/3\underline{I} \rangle \tag{61}$$

Based on the above, the projection of $\underline{S}$ follows by:

$$\langle \underline{S}, \underline{E}_{shear} \rangle = \langle \langle D^{\otimes 2} \rangle, \underline{E}_{shear} \rangle - \langle \langle D \rangle^{\otimes 2}, \underline{E}_{shear} \rangle = \tag{62}$$

$$= \langle \langle D^{\otimes 2}, \underline{E}_{shear} \rangle \rangle - \langle \langle D \rangle^{\otimes 2}, \underline{E}_{shear} \rangle = \tag{63}$$

$$= \langle V_\lambda(D) \rangle - V_\lambda(\langle D \rangle) \tag{64}$$

As realized by the inventors, $V_{MD}$ can be interpreted as the bulk variation of diffusion tensors (i.e. variation in size) and $\Delta V_\lambda$ as the shear of them (i.e. variation between directions).

In conventional diffusion tensor imaging (DTI), an often considered invariant parameter is the fractional anisotropy (FA). It is defined by the normalized variance of the eigenvalues of the average tensor (see e.g. reference [29])

$$FA(\langle D \rangle) = \sqrt{\frac{3}{2} \frac{\frac{1}{3}\sum_{i=1}^{3}\lambda_i^2 - \left(\frac{1}{3}\sum_{i=1}^{3}\lambda_i\right)^2}{\frac{1}{3}\sum_{i=1}^{3}\lambda_i^2}} \tag{65}$$

By utilizing Eqs. (44-48) and (54-56), the FA may be expressed as projections of the conventional average diffusion tensor, raised to a higher order by taking the outer product with itself, on the bulk and shear bases according to $$FA(\langle D \rangle) = \sqrt{\frac{3}{2}\left(1 + \frac{\langle \langle D \rangle^{\otimes 2}, \underline{E}_{bulk} \rangle}{\langle \langle D \rangle^{\otimes 2}, \underline{E}_{shear} \rangle}\right)^{-1}} \tag{66}$$

$$= \sqrt{\frac{3}{2}\left(1 + \frac{MD(\langle D \rangle)^2}{V_\lambda(\langle D \rangle)}\right)^{-1}}$$

Hence, by replacing the variance of the average diffusion tensor, $V_\lambda(\langle D \rangle)$, with the average variance of the eigenvalues of the microscopic compartment tensors (i.e. of the diffusion tensors of the partial volumes of the portion of the sample), $\langle V_\lambda(D) \rangle$, the microscopic FA (μFA) may be obtained according to $$\mu FA = \sqrt{\frac{3}{2}\left(1 + \frac{\langle D \rangle^{\otimes 2}, \underline{E}_{bulk} \rangle}{\langle D \rangle^{\otimes 2}, \underline{E}_{shear} \rangle}\right)^{-1}} \tag{67}$$

where $\langle \mathbf{D}^{\otimes 2} \rangle = \underline{S} + \langle \mathbf{D} \rangle^{\otimes 2}$. If all microscopic tensors share the same set of eigenvalues they share the same value of $V_\lambda(D)$, and in that case μFA will yield the exact FA of the microscopic tensors.

By calculating the μFA using Equation (67), the parameter becomes insensitive to orientation dispersion since the outer product in the μFA calculation acts on the local diffusion tensor, not the globally averaged tensor. This also allows for simple implementation and estimation.

Voigt Notation of Tensors

For implementation purposes, the tensors D and S may advantageously be represented in Voigt notation, which allows D to be represented as a column vector of size 6×1

$$d = (D_{xx}, D_{yy}, D_{zz}, \sqrt{2}D_{yz}, \sqrt{2}D_{xz}, \sqrt{2}D_{xy})^T. \tag{68}$$

The fourth order 4th-order tensor $\underline{S}$ can now be represented by a 6×6 variance-covariance matrix, defined in terms of d according to $$\underline{S} = \langle dd^T \rangle - \langle d \rangle \langle d \rangle^T, \tag{69}$$

since $\mathbf{D}^{\otimes 2} = dd^T$. In full, $\underline{S}$ is given by $$S = \begin{pmatrix} \sum_{xxxx} & \sum_{xxyy} & \sum_{xxzz} & \sqrt{2}\sum_{xxyz} & \sqrt{2}\sum_{xxxz} & \sqrt{2}\sum_{xxxy} \\ \sum_{yyxx} & \sum_{yyyy} & \sum_{yyzz} & \sqrt{2}\sum_{yyyz} & \sqrt{2}\sum_{yyxz} & \sqrt{2}\sum_{yyxy} \\ \sum_{zzxx} & \sum_{zzyy} & \sum_{zzzz} & \sqrt{2}\sum_{zzyz} & \sqrt{2}\sum_{zzxz} & \sqrt{2}\sum_{zzxy} \\ \sqrt{2}\sum_{yzxx} & \sqrt{2}\sum_{yzyy} & \sqrt{2}\sum_{yzzz} & 2\sum_{yzyz} & 2\sum_{yzxz} & 2\sum_{yzxy} \\ \sqrt{2}\sum_{xzxx} & \sqrt{2}\sum_{xzyy} & \sqrt{2}\sum_{xzzz} & 2\sum_{xzyz} & 2\sum_{xzxz} & 2\sum_{xzxy} \\ \sqrt{2}\sum_{xyxx} & \sqrt{2}\sum_{xyyy} & \sqrt{2}\sum_{xyzz} & 2\sum_{xyyz} & 2\sum_{xyxz} & 2\sum_{xyxy} \end{pmatrix} \quad (70)$$

A tensor of rank four, such as $\underline{B}$, may either be represented by a 6×6 matrix (analogous to Equation (70)), $B = \mathbf{b}^{\otimes 2} = \mathbf{b}_V \mathbf{b}_V^T$, or in Voigt notation by a 21×1 column vector $\underline{b}$ according to:

$$\underline{b} = \begin{pmatrix} \sqrt{1}\, b_{xx} b_{xx} \\ \sqrt{1}\, b_{yy} b_{yy} \\ \sqrt{1}\, b_{zz} b_{zz} \\ \sqrt{2}\, b_{yy} b_{zz} \\ \sqrt{2}\, b_{xx} b_{zz} \\ \sqrt{2}\, b_{xx} b_{yy} \\ \sqrt{4}\, b_{xx} b_{yz} \\ \sqrt{4}\, b_{xx} b_{xz} \\ \sqrt{4}\, b_{xx} b_{xy} \\ \sqrt{4}\, b_{yy} b_{yz} \\ \sqrt{4}\, b_{yy} b_{xz} \\ \sqrt{4}\, b_{yy} b_{xy} \\ \sqrt{4}\, b_{zz} b_{yz} \\ \sqrt{4}\, b_{zz} b_{xz} \\ \sqrt{4}\, b_{zz} b_{xy} \\ \sqrt{4}\, b_{yz} b_{yz} \\ \sqrt{4}\, b_{xz} b_{xz} \\ \sqrt{4}\, b_{xy} b_{xy} \\ \sqrt{8}\, b_{yz} b_{xz} \\ \sqrt{8}\, b_{xz} b_{xy} \\ \sqrt{8}\, b_{xy} b_{yz} \end{pmatrix} \quad (71)$$

Using Voigt notation the bulk and shear bases may be represented by:

$$E_{bulk} = \frac{1}{9} \begin{pmatrix} 1 & 1 & 1 & 0 & 0 & 0 \\ 1 & 1 & 1 & 0 & 0 & 0 \\ 1 & 1 & 1 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \end{pmatrix} \quad (72)$$

and $$E_{shear} = \frac{1}{9} \begin{pmatrix} 2 & -1 & -1 & 0 & 0 & 0 \\ -1 & 2 & -1 & 0 & 0 & 0 \\ -1 & -1 & 2 & 0 & 0 & 0 \\ 0 & 0 & 0 & 3 & 0 & 0 \\ 0 & 0 & 0 & 0 & 3 & 0 \\ 0 & 0 & 0 & 0 & 0 & 3 \end{pmatrix} \quad (73)$$

As indicated above, these two isotropic bulk and shear bases are by design orthogonal, and as can be noted from Eqs. (45) and (46), adding these basis functions gives the simple structure of the diagonal identity matrix.

Inner and Outer Products

One advantage of using matrix and vector representations of the tensors in implementations is that inner and outer products become straightforward to implement in software. The outer product of a tensor (e.g. D) may be calculated according to $$\mathbf{D}^{\otimes 2} = \mathrm{d}\mathrm{d}^T \quad (74)$$

One may thus define, for example, $N = \mathbf{n}^{\otimes 2}$ or in Voigt notation $n = \mathbf{n}^{\otimes 2}$.

Inner products are represented by $\langle \bullet, \bullet \rangle$, and may be defined as an element-wise multiplication followed by summation according to $$\langle D, N \rangle = \mathrm{d}^T \mathrm{n} \quad (75)$$

or $$\langle \underline{S}, \underline{B} \rangle = \underline{s}^T \underline{b} \quad (76)$$

The inner product of two matrices may also be defined according to $$\langle D, N \rangle = Tr(DN^T) \quad (77)$$

Description of Embodiments

Taking the above into account, according to a preferred embodiment, a plurality of diffusion weighted echo attenuation measurements are performed on the sample using a plurality of different diffusion encoding magnetic gradient pulse sequences, wherein each magnetic gradient pulse sequence $G_i$ is generated such that a diffusion encoding tensor $b_i$ for the magnetic gradient pulse sequence $G_i$. The plurality of pulse sequences may include a combination of pulse sequences with diffusion encoding tensors having 1 to 3, and preferably 2 to 3, non-zero eigenvalues. The above discussion concerning implementation of the method on an NMR spectroscope or MRI device applies also to the present embodiment.

In a general case the q-vector may be built up by a time-dependent gradient to traverse an arbitrary path in q-space. The rank (i.e. the number of non-zero eigenvalues)

of the diffusion encoding tensor depends on the path, and becomes 1 in the case of sPFG, 2 for dPFG when the first and the second gradient pulse are applied along orthogonal directions, and 3 in the isotropic encoding case such as the triple-PFG [4] or q-MAS [30]. For example, a planar diffusion encoding tensor, i.e. an encoding that is rotationally symmetric in the plane can be achieved by a set of time varying gradients that produce a planar q-space trajectory. Constant angular b-value encoding can be ensured by varying the speed of the traversal in q-space, by using slower speed at low q-values, since the b-value is a function of both time and q-value. At a low q, a long diffusion time can build up the same encoding power (b-value), as a higher q-value with a shorter diffusion time.

A set of data $\{E_1, \ldots E_m\}$ representing the echo attenuation measurements acquired using the pulse sequences $G_i$ may be collected and arranged in a column vector representation. b and $\langle D \rangle$ may (using Voigt notation) be arranged in column vector representations of size 6×1, denoted by $b_V$ and $\langle d \rangle$, and similarly, the fourth-order tensors $\underline{B}$ and $\underline{S}$ may be arranged as column vector representations of size 21×1, denoted by $\underline{b}$ and $\underline{s}$. The elements of each $b_i$ may be obtained using the definitions in Eqs. (5) and (8). The inner products in Eq. (37) can now be expressed by simple matrix operations according to $$\langle b, \langle D \rangle \rangle = b_V^T \langle d \rangle \tag{78}$$

and $$\langle \underline{B}, \underline{S} \rangle = \underline{b}^T \underline{s} \tag{79}$$

Since Eq. (37) is a linear model, $\langle d \rangle$ and $\underline{s}$ may be estimated using pseudoinversion to solve the following equation system $$\begin{pmatrix} \log E_1 \\ \vdots \\ \log E_m \end{pmatrix} = \begin{pmatrix} 1 & -b_{V1}^T & \frac{1}{2} \underline{b}_1^T \\ \vdots & \vdots & \vdots \\ 1 & -b_{Vm}^T & \frac{1}{2} \underline{b}_m^T \end{pmatrix} (E_0 \ \langle d \rangle \ \underline{s})^T \tag{80}$$

Equation (80) forms a linear system of equations based on the cumulant expansion of Equation (36). The data $\{E_1, \ldots E_m\}$ forms constants of the linear system. The diffusion encoding tensor representations $b_{V1\ldots m}$ of the pulse sequences $G_i$ and the fourth-order tensor representations $\underline{b}_{1\ldots m}$ thereof form parameters of the linear system.

In total, the model has 1+6+21=28 free parameters in $E_0$, $\langle d \rangle$, and $\underline{s}$. To enable estimation of a solution to Equation (80) using pseudoinversion, the data should be acquired with measurement tensors of varying shapes, such that the correlation between bulk component $(\underline{b}_k^T \underline{e}_{bulk})$ and shear component $(\underline{b}_k^T \underline{e}_{shear})$ become less than unity. This explains why separation of the two isotropic components of $\underline{S}$ would not be possible with conventional sPFG. Assuming that the bulk and shear components of the encoding tensors are not fully correlated, the pseudoinversion may be performed if the number of measurements exceeds 28. However, fewer measurements can be used if only projections of $\langle d \rangle$, and $\underline{s}$ are sought for.

In the above the inventive concept has mainly been described with reference to a limited number of examples. However, as is readily appreciated by a person skilled in the art, other examples than the ones disclosed above are equally possible within the scope of the inventive concept, as defined by the appended claims.

LIST OF REFERENCES

In the above disclosure, one or more numbers between a pair of brackets "[ ]" refer to a correspondingly numbered reference document in the following list of references:

[1] P. T. Callaghan, O. Söderman, Examination of the lamellar phase of Aerosol OT/water using pulsed field gradient nuclear magnetic resonance, J. Phys. Chem., 87 (1983) 1737-1744.

[2] M. E. Moseley, J. Kucharczyk, H. S. Asgari, D. Norman, Anisotropy in diffusion-weighted MRI, Magn. Reson. Med., 19 (1991) 321-326.

[3] E. O. Stejskal, J. E. Tanner, Spin diffusion measurements: Spin echoes in the presence of a time-dependent field gradient, J. Chem. Phys., 42 (1965) 288-292.

[4] S. Eriksson, S. Lasic, D. Topgaard, Isotropic diffusion weighting in PGSE NMR by magic-angle spinning of the q-vector, J. Magn. Reson., 226 (2013) 13-18.

[5] L. Frydman, G. C. Chingas, Y. K. Lee, P. J. Grandinetti, M. A. Eastman, G. A. Barrall, A. Pines, Variable-angle correlation spectroscopy in solid-state nuclear magnetic resonance, J. Chem. Phys., 97 (1992) 4800-4808.

[6] A. Bax, N. M. Szeverenyi, G. E. Maciel, Chemical shift anisotropy in powdered solids studied by 2D FT NMR with flipping of the spinning axis, J. Magn. Reson., 55 (1983) 494-497.

[7] Y.-Q. Song, L. Venkataramanan, M. D. Hurlimann, M. Flaum, P. Frulla, C. Straley, T1-T2 correlation spectra obtained using a fast two-dimensional Laplace inversion, J. Magn. Reson., 154 (2002) 261-268.

[8] M. Lustig, D. Donoho, J. M. Pauly, Sparse MRI: The application of compressed sensing for rapid MR imaging, Magn. Reson. Med., 58 (2007) 1182-1195.

[9] M. Mobli, M. W. Maciejewski, A. D. Schuyler, A. S. Stern, J. C. Hoch, Sparse sampling methods in multidimensional NMR, Phys. Chem. Chem. Phys., 14 (2012) 10835-10843.

[10] D. Topgaard, Isotropic diffusion weighting in PGSE NMR: Numerical optimization of the q-MAS PGSE sequence, Microporous Mesoporous Mater., 178 (2013) 60-63.

[11] P. J. Basser, J. Mattiello, D. Le Bihan, MR diffusion tensor spectroscopy and imaging, Biophys. J., 66 (1994) 259-267.

[12] K. Schmidt-Rohr, H. W. Spiess, Multidimensional solid-state NMR and polymers, Academic Press, San Diego, (1994).

[13] M. Duer, Introduction to solid-state NMR spectroscopy, Blackwell Publishing Ltd, Oxford, (2004).

[14] W. S. Price, NMR studies of translational motion, Cambridge University Press, Cambridge, (2009).

[15] P. T. Callaghan, Translational dynamics & magnetic resonance, Oxford University Press, Oxford, (2011).

[16] G. B. Arfken, H.-J. Weber, Mathematical methods for physicists, 4th ed., Academic Press, San Diego, (1995).

[17] V. J. Wedeen, D. L. Rosene, R. Wang, G. Dai, F. Mortazavi, P. Hagmann, J. H. Kaas, W.-Y. I. Tseng, The geometric structure of the brain fiber pathways, Science, 335 (2012) 1628-1634.

[18] K. P. Whittal, Analysis of large one-dimensional and two-dimensional relaxation data sets, J. Magn. Reson. A, 110 (1994) 214-218.

[19] D. Bernin, D. Topgaard, NMR diffusion and relaxation correlation methods: New insights in heterogeneous materials, Curr. Opin. Colloid Interface Sci., 18 (2013) 166-172.

[20] J. Mitchell, T. C. Chandrasekera, L. F. Gladden, Numerical estimation of relaxation and diffusion distributions in two dimensions, Prog. Nucl. Magn. Reson. Spectrosc., 62 (2012) 34-50.

[21] B. Jönsson, B. Lindman, K. Holmberg, B. Kronberg, Surfactants and polymers in aqueous solution, John Wiley & Sons Ltd, (1998).

[22] M. Bak, N. C. Nielsen, REPULSION, A novel approach to efficient powder averaging in solid-state NMR, J. Magn. Reson., 125 (1997) 132-139.

[23] D. K. Jones, M. A. Horsfield, A. Simmons, Optimal strategies for measuring diffusion in anisotropic systems by magnetic resonance imaging, Magn. Reson. Med., 42 (1999) 515-525.

[24] Le Bihan, D., J.B.H.: Diffusion MRI at 25: exploring brain tissue structure and function (2012)

[25] Assaf, Y., P.O.: Diffusion MRI at 25: exploring brain tissue structure and function (2008)

[26] Jones, D. K., K.T.R.T.R.: White matter integrity, fiber count, and other fallacies: the dos and don't's of diffusion mri (2013)

[27] Vos, S. B., J.D.K.J.B.V.M.A.L.A.: The influence of complex white matter architecture on the mean diffusivity in diffusion tensor mri of the human brain (2012)

[28] Moakher, M.: Fourth-order cartesian tensors: old and new facts, notions and applications. The Quart. Jour. of Mechanics and Applied Math. 61(2) (2008) 181-203

[29] Basser, P. J., Pierpaoli, C.: Microstructural and physiological features of tissues elucidated by quantitative-diffusion-tensor mri. Journal of Magnetic Resonance, Series B 111(3) (1996) 209-219

[30] Valette, J., Giraudeau, C., Marchadour, C., Djemai, B., Geffroy, F., Ghaly, M. A., Le Bihan, D., Hantraye, P., Lebon, V., Lethimonnier, F.: A new sequence for single-shot diffusion-weighted nmr spectroscopy by the trace of the diffusion tensor. MRM 68(6) (2012) 1705-1712

The invention claimed is:

1. A method for quantifying isotropic diffusion and/or anisotropic diffusion in a sample, the method comprising:
    performing diffusion weighted magnetic resonance measurements on the sample using diffusion encoding magnetic gradient pulse sequences $G_{i=1 \ldots m}$, wherein each magnetic gradient pulse sequence $G_i$ is generated such that a diffusion encoding tensor $b_i$ for the magnetic gradient pulse sequence $G_i$ has one to three non-zero eigenvalues, where $$b_i = \int_0^\tau q_i(t) q_i^T(t) dt,$$

$q_i$ (t) is a dephasing vector proportional to $$\int_0^t G_i(t') dt'$$

$q_i^T$ (t) is a transpose of the dephasing vector $q_i$ (t), and $\tau$ is an echo time,
collecting data representing magnetic resonance echo signal measurements, at least a subset of said data representing echo signals being acquired with a set of magnetic gradient pulse sequences causing anisotropic diffusion weighting, wherein the diffusion encoding tensor for each gradient pulse sequence of said set of magnetic gradient pulse sequences has three non-zero eigenvalues, at least one of the three eigenvalues being different from the other eigenvalues, and
calculating a degree of isotropic diffusion and/or a degree of anisotropic diffusion using said data.

2. A method according to claim 1, wherein said subset of data represents echo signals from a portion of the sample, said portion including a plurality of partial volumes presenting different degrees of isotropic diffusion or different degrees and/or different orientations of anisotropic diffusion, wherein the calculation of a degree of isotropic diffusion and/or a degree of anisotropic diffusion includes calculation of an estimate of a degree of isotropic diffusion and/or an estimate of a degree of anisotropic diffusion for at least one of said partial volumes.

3. A method according to claim 1,
wherein said set of magnetic gradient pulse sequences forms a first set of magnetic gradient pulse sequences and said subset of data forms a first subset of data representing a first echo attenuation curve acquired with the first set of magnetic gradient pulse sequences, and
wherein said data further includes at least a second subset of data representing a second echo attenuation curve acquired with a second set of magnetic gradient pulse sequences causing isotropic or anisotropic diffusion weighting.

4. A method according to claim 3,
wherein each pulse sequence of the first set is such that a first eigenvalue and a second eigenvalue of the diffusion encoding tensor for said pulse sequence are equal to each other, and
wherein each pulse sequence of the second set is such that a first and a second eigenvalue of the diffusion encoding tensor for said pulse sequence are equal to each other.

5. A method according to claim 4,
wherein the pulse sequences of the first set and the second set of magnetic gradient pulse have varying maximum gradient magnitudes.

6. A method according to claim 3,
wherein, for each pulse sequence of the first set there is a first diffusion encoding tensor invariant $\Delta_{b,1}$ definable by:

$$\Delta_{b,1} = \frac{1}{b}\left(b_{zz}^{PAS} - \frac{b_{yy}^{PAS} + b_{xx}^{PAS}}{2}\right), b = b_{xx}^{PAS} + b_{yy}^{PAS} + b_{zz}^{PAS}$$

where $b_{xx}^{PAS}$ represents a first eigenvalue of the diffusion encoding tensor for said pulse sequence, $b_{yy}^{PAS}$ represents a second eigenvalue of the diffusion encoding tensor for said pulse sequence and $b_{zz}^{PAS}$ represents a third eigenvalue of the diffusion encoding tensor for said pulse sequence, and
wherein the first set of pulse sequences is such that the first diffusion encoding tensor invariant $\Delta_{b,1}$ of the pulse sequences of the first set are equal to each other.

7. A method according to claim 6,
wherein, for each pulse sequence of the second set there is a second diffusion encoding tensor invariant $\Delta_{b,2}$ definable by:

$$\Delta_{b,2} = \frac{1}{b}\left(b_{zz}^{PAS} - \frac{b_{yy}^{PAS} + b_{xx}^{PAS}}{2}\right), b = b_{xx}^{PAS} + b_{yy}^{PAS} + b_{zz}^{PAS}$$

where $b_{xx}^{PAS}$ represents a first eigenvalue of the diffusion encoding tensor for said pulse sequence, $b_{yy}^{PAS}$ represents the second eigenvalue of the diffusion encoding tensor for said pulse sequence and $b_{zz}^{PAS}$ represents a third eigenvalue of the diffusion encoding tensor for said pulse sequence, and wherein the second set of pulse sequences is such that the second diffusion encoding tensor invariant $\Delta_{b,2}$ of the pulse sequences of the second set are equal to each other and $\Delta_{b,2}$ is different from $\Delta_{b,1}$.

8. A method according to claim 3, wherein calculating a degree of isotropic diffusion and/or a degree of anisotropic diffusion includes:
calculating a degree of isotropic diffusion and/or a degree of anisotropic diffusion by analyzing a change, a variation or a difference between a first echo signal acquired with a pulse sequence of the first set and a second echo signal acquired with a pulse sequence of the second set.

9. A method according to claim 3, wherein, in addition to the first subset of said data and the second subset of said data, said data includes at least a third subset of data acquired with a third set of magnetic gradient pulse sequences causing anisotropic diffusion weighting,
wherein the diffusion encoding tensor for each gradient pulse sequence of the third set has 3 non-zero eigenvalues of which a first eigenvalue and a second eigenvalue are equal to each other and different from a third eigenvalue, and
wherein, for each pulse sequence of the third set there is a third diffusion encoding tensor invariant $\Delta_{b,3}$ definable by:

$$\Delta_{b,3} = \frac{1}{b}\left(b_{zz}^{PAS} - \frac{b_{yy}^{PAS} + b_{xx}^{PAS}}{2}\right), b = b_{xx}^{PAS} + b_{yy}^{PAS} + b_{zz}^{PAS}$$

where $b_{xx}^{PAS}$ represents a first eigenvalue of the diffusion encoding tensor for said pulse sequence, $b_{yy}^{PAS}$ represents the second eigenvalue of the diffusion encoding tensor for said pulse sequence and $b_{zz}^{PAS}$ represents a third eigenvalue of the diffusion encoding tensor for said pulse sequence, and wherein the third set of pulse sequences is such that the third diffusion encoding tensor invariant $\Delta_{b,3}$ of the pulse sequences of the third set are equal to each other and $\Delta_{b,3}$ is different from $\Delta_{b,2}$ and $\Delta_{b,1}$.

10. A method according to claim 9, wherein each pulse sequence of the first set is such that $\Delta_{b,1}>0$, each pulse sequence of the second set is such that $\Delta_{b,2}=0$, and each pulse sequence of the third set is such that $\Delta_{b,3}<0$.

11. A method according to claim 3, further comprising:
calculating, based on the data representing said echo signals, a probability distribution indicating a probability of each one of said echo signals being associated with each one of a plurality of different values of a model isotropic diffusion parameter $D_{iso}$ and/or a model anisotropic diffusion parameter $\Delta_D$.

12. A method according to claim 11, wherein said probability distribution is calculated by determining a solution to a system of equations relating the echo signals represented by said data to a product of a kernel function and said probability distribution.

13. A method according to claim 12, wherein said probability distribution is a joint probability distribution and said kernel function is a matrix including at least M×N elements, each of said elements being based on an integration of $$\exp(-bD_{iso})\cdot\exp\left(\frac{A}{3}\right)\cdot\frac{\sqrt{\pi}}{2}\frac{\gamma(1/2, A)}{\sqrt{A}}, \text{ where } A = 3bD_{iso}\Delta_b\Delta_D$$

and Y is the magnetogyric ratio, for a combination of values of a diffusion weighting magnitude b, a diffusion encoding tensor invariant $\Delta_b$, the model isotropic diffusion parameter $D_{iso}$ and the model anisotropic diffusion parameter $\Delta_D$.

14. A method according to claim 1, further comprising:
applying each pulse sequence of said first set of magnetic gradient pulse sequences a plurality of times to the sample, with different orientations of the gradient pulse with respect to a fixed laboratory frame, and
forming said first subset of data by averaging echo attenuation measurements acquired for said different orientations.

15. A method according to claim 1, wherein each one of said diffusion encoding magnetic gradient pulse sequences $G_i$ forms part of a triple stimulated echo sequence.

16. A method according to claim 3, further comprising:
forming a system of equations based on an expansion of a function relating an echo signal E to a diffusion encoding tensor b and a diffusion tensor D,
calculating an average diffusion tensor <D> and a diffusion tensor covariance tensor $\underline{S}$ by determining a solution to the system of equations using echo signal measurements represented by said data and representations of at least a subset of the diffusion encoding tensors $b_i$,
calculating an invariant bulk component $S_{bulk}$ of the covariance tensor $\underline{S}$ by projecting $\underline{S}$ onto a bulk basis $\underline{E}_{bulk}$,
calculating an invariant shear component $S_{shear}$ of the covariance tensor $\underline{S}$ by projecting $\underline{S}$ onto a shear basis $\underline{E}_{shear}$,
calculating a degree of isotropic diffusion and/or a degree of anisotropic diffusion using the invariant bulk component $S_{bulk}$ and/or the invariant shear component $S_{shear}$.

17. A method according to claim 16, wherein the system of equations is equivalent to a cumulant expansion of the function $E(b)=\langle\exp(-\langle b,D\rangle)\rangle$.

18. A method according to claim 16, wherein the degree of anisotropic diffusion is calculated based on a sum of the invariant shear component $S_{shear}$ and a projection of the square of the average diffusion tensor <D> onto the shear basis $\underline{E}_{shear}$.

19. A method according to claim 18, wherein the degree of anisotropic diffusion is calculated based on a ratio between a projection of the square of the average diffusion tensor <D> onto the bulk basis $\underline{E}_{bulk}$ and said sum.

20. A method according to claim 19, wherein the degree of anisotropic diffusion is calculated as an estimate of a microscopic fractional anisotropy μFA based on said ratio.

* * * * *